US008541456B2

(12) United States Patent
Kley et al.

(10) Patent No.: US 8,541,456 B2
(45) Date of Patent: *Sep. 24, 2013

(54) ROFLUMILAST FOR THE TREATMENT OF DIABETES MELLITUS TYPE 2

(75) Inventors: Hans-Peter Kley, Allensbach (DE); Guido Hanauer, Constance (DE); Daniela Hauser, Singen (DE); Beate Schmidt, Allensbach (DE); Dirk Bredenbröker, Constance (DE); Wilhelm Wurst, Constance (DE); Jörg Kemkowski, Hamburg (DE)

(73) Assignee: Takeda GmbH, Constance (DE)

( * ) Notice: Subject to any disclaimer, the term of this patent is extended or adjusted under 35 U.S.C. 154(b) by 0 days.

This patent is subject to a terminal disclaimer.

(21) Appl. No.: 13/179,895

(22) Filed: Jul. 11, 2011

(65) Prior Publication Data

US 2011/0269750 A1 Nov. 3, 2011

Related U.S. Application Data

(63) Continuation of application No. 11/885,450, filed as application No. PCT/EP2006/060418 on Mar. 3, 2006, now Pat. No. 8,017,633.

(30) Foreign Application Priority Data

Aug. 3, 2005 (EP) .................................. 05101772

(51) Int. Cl.
*A61K 31/44* (2006.01)
*A61K 31/19* (2006.01)

(52) U.S. Cl.
USPC ............ 514/352; 514/342; 514/571; 514/866

(58) Field of Classification Search
USPC .................. 514/352, 571, 342, 866
See application file for complete search history.

(56) References Cited

U.S. PATENT DOCUMENTS

| | | | |
|---|---|---|---|
| 3,174,901 A | | 3/1965 | Sterne |
| 4,687,777 A | * | 8/1987 | Meguro et al. ................ 514/342 |
| 5,712,298 A | | 1/1998 | Amschler |
| 5,730,975 A | | 3/1998 | Hotamisligil et al. |
| 5,817,670 A | | 10/1998 | Takayama et al. |
| 6,011,060 A | | 1/2000 | Laurent et al. |
| 6,191,138 B1 | | 2/2001 | Gutterer |
| 6,255,326 B1 | | 7/2001 | Ashton et al. |
| 6,258,850 B1 | * | 7/2001 | Andersson ................ 514/571 |
| 6,331,543 B1 | | 12/2001 | Garvey et al. |
| 6,448,274 B2 | * | 9/2002 | Friesen et al. ................ 514/352 |
| 6,699,871 B2 | | 3/2004 | Edmondson et al. |
| 6,924,292 B2 | | 8/2005 | Kawano et al. |
| 7,109,342 B2 | | 9/2006 | Nakai et al. |
| 7,776,893 B2 | | 8/2010 | Kley |
| 8,017,633 B2 | * | 9/2011 | Kley et al. .................... 514/352 |
| 2002/0002191 A1 | | 1/2002 | Friesen et al. |
| 2002/0002192 A1 | | 1/2002 | Chen et al. |
| 2003/0023087 A1 | | 1/2003 | Garvey et al. |
| 2003/0069169 A1 | | 4/2003 | Macor et al. |
| 2003/0100563 A1 | | 5/2003 | Edmondson et al. |
| 2003/0186974 A1 | | 10/2003 | Marfat et al. |
| 2004/0087591 A1 | | 5/2004 | Garvey et al. |
| 2004/0235845 A1 | | 11/2004 | Eggenweiler et al. |
| 2005/0049258 A1 | | 3/2005 | Marfat et al. |
| 2005/0130891 A1 | | 6/2005 | Forssmann et al. |
| 2006/0281745 A1 | | 12/2006 | Kley |

FOREIGN PATENT DOCUMENTS

| | | |
|---|---|---|
| CA | 2 542 277 A1 | 5/2005 |
| DE | 10150517 A1 | 4/2003 |
| EP | 0300726 B1 | 9/1993 |
| JP | 58-69812 A | 4/1983 |
| WO | 94/02150 A1 | 2/1994 |
| WO | 94/02465 A1 | 2/1994 |
| WO | 95/01338 A1 | 1/1995 |
| WO | 97/28131 A1 | 8/1997 |
| WO | 99/14239 A1 | 3/1999 |
| WO | 00/42020 A1 | 7/2000 |
| WO | 00/42034 A1 | 7/2000 |
| WO | 01/35979 A2 | 5/2001 |
| WO | 01/42244 A1 | 6/2001 |
| WO | 01/70746 A1 | 9/2001 |
| WO | 01/90076 A1 | 11/2001 |
| WO | 02/13798 A2 | 2/2002 |
| WO | 02/14280 A1 | 2/2002 |
| WO | 02/064584 A1 | 8/2002 |
| WO | 02/074726 A2 | 9/2002 |
| WO | 03/032993 A1 | 4/2003 |
| WO | 03/061638 A2 | 7/2003 |
| WO | 03/099334 A1 | 12/2003 |
| WO | 2004/016596 A1 | 2/2004 |
| WO | 2004/067006 A1 | 8/2004 |
| WO | 2004/098595 A1 | 11/2004 |
| WO | 2004/098596 A1 | 11/2004 |
| WO | 2004/098597 A1 | 11/2004 |
| WO | 2004/098598 A1 | 11/2004 |
| WO | 2004/101752 A2 | 11/2004 |
| WO | 2004/103407 A2 | 12/2004 |
| WO | 2005/020926 A2 | 3/2005 |
| WO | 2005/041864 A2 | 5/2005 |
| WO | 2005/116653 A2 | 12/2005 |

OTHER PUBLICATIONS

Gerich, "Postprandial Hyperglycemia and Cardiovascular Disease", Endocrine Practice, vol. 12, Suppl. 1, pp. 47-51, (2006).
Liang, et al., "The Phosphodiesterase Inhibitors Pentoxifylline and Rolipram Prevent Diabetes in NOD Mice", Diabetes, 47:570-575, 1998.
Leibowitz, et al., "A Novel Insulin Secretagogue is a Phosphodiesterase Inhibitor", Diabetes, 44:67-74, 1995.
Ceriello, et al., "Postprandial Glucose Regulation and Diabetic Complications", Arch. Intern. Med., 164: 2090-2095, 2004.

* cited by examiner

*Primary Examiner* — Kevin E Weddington
(74) *Attorney, Agent, or Firm* — Nath, Goldberg & Meyer; Sheldon M. McGee

(57) ABSTRACT

The application relates to specific combinations of Roflumilast and/or Roflumilast N-Oxide and a PPAR-agonist, as well as their use in the treatment of diabetes mellitus type 2.

8 Claims, No Drawings

ROFLUMILAST FOR THE TREATMENT OF DIABETES MELLITUS TYPE 2

This application is a continuation application of U.S. Ser. No. 11/885,450, filed Sep. 5, 2007, which is a continuation application of PCT/EP2006/060418, filed Mar. 3, 2006.

TECHNICAL FIELD

The invention relates to the use of Roflumilast, its pharmacologically acceptable salts, its N-Oxide and the pharmacologically acceptable salts of the latter for the treatment of diabetes mellitus type 2, diabetes mellitus type 1 and for the prevention and/or inhibition of the progression of disorders which are related to diabetes mellitus.

The invention furthermore relates to combinations of Roflumilast, its pharmacologically acceptable salts, its N-Oxide and the pharmacologically acceptable salts of the latter with one or more other active compounds which are used in the treatment of diabetes mellitus type 2 and/or diabetes mellitus type 1; as well as to pharmaceutical compositions, combination products and kits containing these combinations and uses of such combinations in the treatment of diabetes mellitus type 2 and/or diabetes mellitus type 1.

BACKGROUND OF THE INVENTION

In the International Patent Application WO99/14239 compositions for treating diabetes mellitus and obesity are disclosed. The compositions contain at least two of the active agents A, B and C, wherein A is at least one hormone which stimulates the production of cAMP, B is at least one substance which inhibits the breakdown of a cyclic nucleotide, and C is at least one hormone which stimulates the production of cGMP. In the International Patent Application WO01/35979 the combined use of a PDE3 and a PDE4 inhibitor for the treatment of obesity is disclosed. In the International Patent Application WO02/13798 the use of a selective cGMP PDE5 inhibitor for the treatment of Insulin Resistance Syndrome is disclosed, wherein the Insulin Resistance Syndrome is defined as the concomitant existence of two or more disease states selected from dyslipidemia, hypertension, type 2 diabetes mellitus, impaired glucose tolerance, a family history of diabetes, hyperuricaemia and/or gout, a pro-coalgulant state, atherosclerosis and truncal obesity. In the unexamined German application DE 10150517 tetrahydropyridazin-3-one derivatives are described which may be useful inter alia for the treatment of diabetes mellitus. In Diabetes 47, pp. 570-575, 1998 is disclosed that pentoxyfylline and rolipram may be effective in the treatment of autoimmune diabetes or other conditions characterized by excessive production of inflammatory cytokines.

Diabetes mellitus is on the rise worldwide and is considered to be at an epidemic level by the World Health Organization. The clinical manifestation and progression of diabetes often vary considerably between countries and commonly between ethnic groups in the same country. Currently diabetes affects 151 million people worldwide and an estimate 300 million people in 2025. There are two main forms of diabetes. Type 1 (insulin-dependent diabetes mellitus, IDDM) is due primarily to autoimmune-mediated destruction of pancreatic β-cells, resulting in absolute insulin deficiency. It is the second most common chronic disease of children. By contrast, type 2 diabetes (non-insulin-dependent diabetes mellitus, NIDDM) is characterized by insulin-resistance and inadequate insulin secretion. A significant fraction of individuals originally diagnosed with type 2 diabetes evolve with time to a type 1 state, which is defined as exhibiting anti-β-cell autoimmunity.

Because genetic factors contribute to the development of diabetes, the disease displays a strong familial aggregation. Although there are monogenic syndromes of insulin resistance, in which a definite gene has been identified as the cause of insulin resistance, these are relative rare. The more common presentation of diabetes appears to be polygenic. Additionally, behavioural- and lifestyle-related risk factors exist. Type 2 diabetes is increasingly common primarily because of increases in the prevalence of a sedentary lifestyle and obesity. One of the major arguments for the role of behavioural factors in the etiology of diabetes has been the rapid increase in the prevalence and incidence of the disease in populations undergoing rapid westernization. The westernization transition is usually accompanied by increases in obesity, decreases in physical activity and alterations in dietary intake toward more calories, fat and non-complex carbohydrates.

Plasma glucose concentrations are normally maintained within a fairly narrow range despite wide fluctuations in the body's supply (e.g. meals) and demand (e.g. exercise) for nutrients. After an overnight fast, insulin-independent tissues, the brain (50%) and splanchnic organs (25%), account for most of the total body glucose disposal. Insulin-dependent tissues, adipose tissue and primarily skeletal muscles, are responsible for the remaining 25% of glucose utilization. This basal glucose uptake is precisely matched by the release of glucose from the liver. In response to hyperglycemia after a meal, pancreatic insulin secretion is stimulated and the combination of hyperinsulinemia plus hyperglycemia promotes glucose uptake (by splanchnic and peripheral, primarily muscle, tissues) and suppresses hepatic glucose production. It follows, therefore, that defects at the level of the β-cell, muscle and liver can lead to the development of glucose intolerance and diabetes mellitus. All the abnormalities in diabetes basically result from an imbalance between insulin sensitivity and insulin secretion. The initial stage of diabetes is characterised by impaired glucose tolerance and postprandial hyperglycemia. As the disease progresses, fasting hyperglycemia is observed.

The earliest detectable abnormality in NIDDM is an impairment in the body's ability to respond to insulin. Because the pancreas is able to appropriately augment its secretion of insulin to offset the insulin resistance, glucose tolerance remains normal. With time, however, the beta-cell fails to maintain its high rate of insulin secretion and the insulin resistance leads to the development of impaired glucose tolerance and eventually overt diabetes mellitus. The cause of pancreatic "exhaustion" remains unknown. Insulin resistance in NIDDM involves both hepatic and peripheral tissues. In response to both endogenously secreted or exogenously administered insulin, hepatic glucose production fails to suppress normally and muscle glucose uptake is diminished. The accelerated rate of hepatic glucose output is due mainly to augmented gluconeogenesis. In muscle many cellular defects in insulin action have been described including impaired insulin-receptor tyrosine kinase activity, diminished glucose transport, and reduced glycogen synthase and pyruvate dehydrogenase activities. The abnormalities account for disturbances in the two major intracellular pathways of glucose disposal, glycogen synthesis and glucose oxidation. In the earliest stages of NIDDM, the major defect involves the inability of insulin to promote glucose uptake and storage as glycogen. Other potential mechanisms that have been put forward to explain the glucose intolerance include increased levels of free fatty acids, chronic low-grade activation of the immune system (increased levels of TNFα and IL6), altered skeletal muscle blood flow, increased conversion of amylin to its insoluble amyloid form and glucose toxicity.

Diabetes is associated with a variety of physiologic disorders such as hypertension and dyslipidemia. Diabetes also increases the risk of macrovascular (coronary artery disease, stroke, amputation) and microvascular (blindness, renal failure, neuropathies) diseases. Myocardial infarction, stroke or renal failure are the cause of death for more than 70% of diabetes patients. The huge mortality and debilitating neuropathies associated with diabetes underline the importance of active medical intervention.

There are several ways to counteract diabetes. The first is lifestyle adjustments aimed at improving endogenous insulin sensitivity. This can be achieved by increased physical activity and bodyweight reduction with diet and behavioural modification. Unfortunately, most people with non-insulin-dependent diabetes mellitus never receive sufficient nutritional education or are not capable of complying with a strict diet regimen.

Another therapeutic way involves increasing insulin availability by the administration of exogenous insulin, insulin analogues and insulin secretagogues such as sulphonylureas. The primary mode of action of sulphonylureas is through the depolarisation of the pancreatic β-cells by blocking the ATP-dependent potassium channels and causing an influx of calcium ions, which stimulate insulin secretion. The most frequently encountered adverse effect of insulin, insulin analogues and insulin secretagogues is hypoglycemia. Body-weight gain can also be a concern, because insulin not only increases uptake of blood glucose but also promotes the synthesis and storage of lipids.

Biguanides, of which metformin is the most commonly used, also have proven to be effective anti-hyperglycemic agents. Metformin reduces hepatic gluconeogenesis and basal hepatic glucose output. Its most serious adverse effect is lactic acidosis. Other common adverse effects of metformin are nausea and anorexia. Oral antidiabetics such as sulphonylureas and metformin as monotherapy or in combination have been shown to decrease fasting plasma glucose levels, but postprandial hyperglycemia persists in more than 60% of patients and probably accounts for sustained increases of hemoglobin $A_{1C}$ levels.

α-Glucosidase inhibitors, e.g. acarbose and miglitol, primarily target postprandial hyperglycemia. The therapy of diabetes mellitus with α-glucosidase inhibitors is based on a delayed intestinal degradation of starch and sucrose. These carbohydrates must be hydrolysed by α-glucosidases to monosaccharides before they can be transported through the mucosa of the small intestine. The reversible inhibition of the brush border glucosidases results in redistribution of carbohydrate absorption from the upper portion of the gut to a more extended surface area covering the whole length of the small intestine. This is accompanied by a delayed absorption of monosaccharides and a decrease in the postprandial elevation of blood glucose. Common adverse effects of α-Glucosidase inhibitors are symptoms of carbohydrate malabsorption and gastrointestinal discomfort.

Another class of antidiabetic drugs are thiazolidinediones, such as rosiglitazone and pioglitazone, which are insulin sensitizers and act through activation of peroxisome proliferator-activated receptor γ (PPARγ). PPARγ is mainly expressed in adipose tissues, plays an important role in adipogenesis and modifies fatty acid synthesis and storage. Binding of rosiglitazone to PPARγ results in reduced endogenous glucose production and increased blood glucose uptake. It increases the sensitivity of skeletal muscle, liver and adipose tissues to insulin. Improvements in glucose metabolism with rosiglitazone treatment are closely correlated with decreased plasma free fatty acid metabolism. The stimulation by rosiglitazone of PPARγ in adipose tissue and subsequent adipocyte differentiation results in the generation of more, but smaller, adipocytes which are more insulin sensitive and produce less free fatty acid, TNFα and leptin. Common adverse effects of rosiglitazone are anemia, oedema and increased body weight.

DESCRIPTION OF THE INVENTION

It is one object of the present invention to make available a pharmaceutical composition for the treatment of diabetes mellitus, in particular diabetes mellitus type 2 which overcomes some or all of the abovementioned disadvantages.

Treatment of diabetes mellitus is surprisingly achieved by the use of a compound of formula 1.1

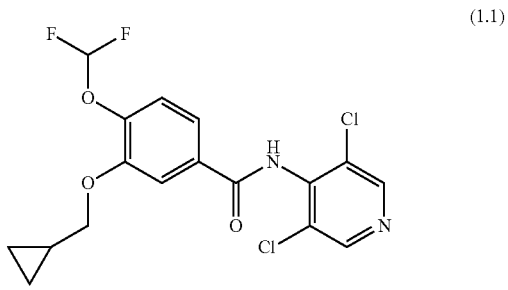 [SMILES: O=C(Nc1c(Cl)cncc1Cl)c1ccc(OC(F)F)c(OCC2CC2)c1]

(1.1)

or a pharmaceutically acceptable salt thereof and/or a compound of formula 1.2

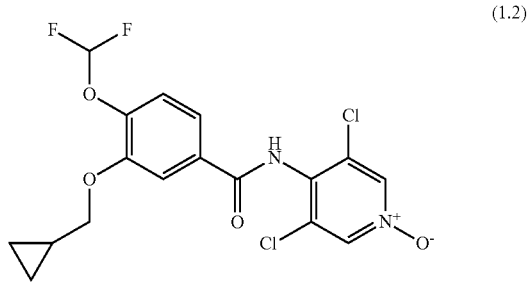 [SMILES: O=C(Nc1c(Cl)c[n+]([O-])cc1Cl)c1ccc(OC(F)F)c(OCC2CC2)c1]

(1.2)

or a pharmaceutically acceptable salt thereof.

The compound of formula 1.1 has the international non-proprietary name (INN) Roflumilast [3-cyclopropyl-methoxy-4-difluoromethoxy-N-(3,5-dichloropyrid-4-yl) benzamide].

The compound of formula 1.2 is Roflumilast-N-Oxide [3-cyclopropylmethoxy-4-difluoromethoxy-N-(3,5-dichloro-1-oxido-pyridin-4-yl)benzamide].

The preparation of Roflumilast, its pharmaceutically acceptable salts and its N-Oxide as well as the use of these compounds as PDE4-inhibitors is described in the international patent application WO95/01338.

Salts encompassed within the term "pharmaceutically acceptable salts" refer to non-toxic salts of the compounds of formulae 1.1 or 1.2 which are generally prepared by reacting a free base with a suitable organic or inorganic acid or by reacting an acid with a suitable organic or inorganic base.

Particular mention may be made of the pharmaceutically acceptable inorganic and organic acids customarily used in pharmacy. Those suitable are in particular water-soluble and water-insoluble acid addition salts with acids such as, for example, hydrochloric acid, hydrobromic acid, phosphoric acid, nitric acid, sulfuric acid, acetic acid, citric acid, D-gluconic acid, benzoic acid, 2-(4-hydroxybenzoyl)-benzoic acid, butyric acid, sulfosalicylic acid, maleic acid, lauric acid, malic acid, fumaric acid, succinic acid, oxalic acid, tartaric acid, embonic acid, stearic acid, toluenesulfonic acid, methanesulfonic acid or 1-hydroxy-2-naphthoic acid. As examples of pharmaceutically acceptable salts with bases may be mentioned the lithium, sodium, potassium, calcium, aluminium, magnesium, titanium, ammonium, meglumine or guanidinium salts.

It is understood that the compounds of formulae 1.1 and 1.2 and their pharmaceutically acceptable salts can also be present in the form of their pharmaceutically acceptable solvates and in particular in the form of their hydrates.

In the expression "diabetes mellitus type 2 and/or type 1 and disorders which are related to diabetes mellitus", diabetes mellitus type 2 stands for non-insulin-dependent diabetes mellitus (NIDDM) and diabetes mellitus type 1 stands for insulin-dependent diabetes mellitus (IDDM). Frequently correlated with diabetes mellitus type 2 are one or more of the metabolic syndrome, obesity, insulin resistance, dyslipidemia and a pathological glucose tolerance. Subjects with diabetes mellitus type 2 and/or type 1 manifest varying degrees of increased blood pressure, increased levels of cholesterol and/or triglycerides, increased levels of uric acid and increased levels of factors that promote coagulation. Therefore disorders which are related to diabetes mellitus are hypertension, hyperlipidemia, hyperuricemia, gout and hypercoagulability, i.e. an abnormal, increased tendency to form clots inside blood vessels. These disorders are well-recognized risk factors for atherosclerotic macrovascular as well as microvascular diseases. Atherosclerotic macrovascular diseases include myocardial infarction, stroke and limb amputation. Microvascular complications involve blindness, renal diseases and debilitating neuropathies.

The term "effective amount" refers to a therapeutically effective amount for treating diabetes mellitus type 2 and/or type 1 or to a therapeutically effective amount for treating diabetes mellitus type 2 and/or type 1 and for the prevention and/or inhibition of the progression of disorders which are related to diabetes mellitus. In case of a combination therapy the term "effective amount" refers to the sum of the amounts of the combination partners, which is therapeutically effective for treating diabetes mellitus type 2 and/or type 1.

"Patient" includes both human and other mammals.

It has now been found that the compound of formula 1.1 and/or the compound of formula 1.2 reduce postprandial hyperglycemia and also fasting hyperglycemia.

This is an advantage over insulin secretagogues, biguanides and α-Glucosidase inhibitors which improve only one of fasting or postprandial hyperglycemia. In contrast to insulin and insulin secretagogues, the compound of formula 1.1 and/or the compound of formula 1.2 do not induce hypoglycemia.

Thus, a first aspect of the present invention is the use of a compound of formula 1.1 or a pharmaceutically acceptable salt thereof and/or a compound of formula 1.2 or a pharmaceutically acceptable salt thereof for the production of a pharmaceutical composition for the treatment of diabetes mellitus type 2 and/or diabetes mellitus type 1.

A further aspect of the present invention is the use of a compound of formula 1.1 or a pharmaceutically acceptable salt thereof and/or a compound of formula 1.2 or a pharmaceutically acceptable salt thereof for the production of a pharmaceutical composition for the treatment of diabetes mellitus type 2 and/or diabetes mellitus type 1 and for the prevention and/or inhibition of the progression of disorders which are related to diabetes mellitus.

Another aspect of the present invention is the use of a compound of formula 1.1 or a pharmaceutically acceptable salt thereof and/or a compound of formula 1.2 or a pharmaceutically acceptable salt thereof for the production of a pharmaceutical composition for the treatment of a disorder selected from the group of metabolic syndrome, obesity, insulin resistance, dyslipidemia and pathological glucose tolerance.

The invention further relates to a method for treating diabetes mellitus type 2 and/or type 1 comprising administering to a patient in need thereof an effective amount of a compound of formula 1.1 or a pharmaceutically acceptable salt thereof and/or a compound of formula 1.2 or a pharmaceutically acceptable salt thereof.

The invention as well relates to a method for treating diabetes mellitus type 2 and/or type 1 and for preventing and/or inhibiting the progression of disorders which are related to diabetes mellitus, comprising administering to a patient in need thereof an effective amount of a compound of formula 1.1 or a pharmaceutically acceptable salt thereof and/or a compound of formula 1.2 or a pharmaceutically acceptable salt thereof.

The invention additionally relates to a method for treating a disorder selected from the group consisting of metabolic syndrome, obesity, insulin resistance, dyslipidemia and pathological glucose tolerance comprising administering to a patient in need thereof an effective amount of a compound of formula 1.1 or a pharmaceutically acceptable salt thereof and/or a compound of formula 1.2 or a pharmaceutically acceptable salt thereof.

Another aspect of the present invention is a method for reducing postprandial hyperglycemia comprising administering to a patient in need thereof for a prolonged period of time an effective amount of a compound of formula 1.1 or a pharmaceutically acceptable salt thereof and/or a compound of formula 1.2 or a pharmaceutically acceptable salt thereof.

Still another aspect of the present invention is a method for reducing fasting hyperglycemia, comprising administering to a patient in need thereof for a prolonged period of time an effective amount of a compound of formula 1.1 or a pharmaceutically acceptable salt thereof and/or a compound of formula 1.2 or a pharmaceutically acceptable salt thereof.

The invention also relates to a method for reducing postprandial hyperglycemia and fasting hyperglycemia, comprising administering to a patient in need thereof for a prolonged period of time an effective amount of a compound of formula 1.1 or a pharmaceutically acceptable salt thereof and/or a compound of formula 1.2 or a pharmaceutically acceptable salt thereof.

The expression "for a prolonged period of time" stands for the repeated administration of the active compound(s) for at least 3 days, more preferably for at least 5 days and most preferably for at least 10 days.

The invention further relates to a ready-to-use pharmaceutical composition, comprising a compound of formula 1.1 or a pharmaceutically acceptable salt thereof and/or a compound of formula 1.2 or a pharmaceutically acceptable salt thereof as active compound(s) [=therapeutic agent(s)], which additionally contains a reference to the fact that this ready to use pharmaceutical composition can be employed in the treatment of diabetes mellitus type 2 and/or type 1 and disorders which are related to diabetes mellitus.

Mode of administration, dosage forms and dosage for the mono-therapy with Roflumilast, Roflumilast-N-oxide or a pharmaceutically acceptable salt of either:

Roflumilast, Roflumilast-N-oxide or a pharmaceutically acceptable salt of either may be administered in a variety of forms. These include, for example, liquid, semi-solid and solid dosage forms, such as liquid solutions (e.g., injectable and infusible solutions), dispersions or suspensions, tablets, pills, powders, liposomes or suppositories. The preferred form depends on the intended mode of administration and therapeutic application.

The most preferred mode of administration of Roflumilast, Roflumilast-N-oxide or a pharmaceutically acceptable salt of either is oral. In another preferred embodiment Roflumilast, Roflumilast-N-oxide or a pharmaceutically acceptable salt of either is administered by intravenous infusion or injection. In a further embodiment the Roflumilast, Roflumilast-N-oxide or a pharmaceutically acceptable salt of either is administered by intramuscular or subcutaneous injection. Other routes of administration are also contemplated, including for example intranasal and transdermal routes, and by inhalation.

Typically, the Roflumilast, Roflumilast-N-oxide or a pharmaceutically acceptable salt of either will be administered in the form of a pharmaceutical composition comprising Roflumilast, Roflumilast-N-oxide or a pharmaceutically acceptable salt of either in conjunction with at least one pharmaceutically acceptable auxiliary.

The pharmaceutical compositions are prepared by processes which are known per se and familiar to the person skilled in the art. As pharmaceutical compositions Roflumilast, Roflumilast-N-oxide or a pharmaceutically acceptable salt of either is either employed as such, or preferably in combination with at least one pharmaceutically acceptable auxiliary, e.g. in the form of tablets, coated tablets, capsules, caplets, suppositories, emulsions, suspensions, gels or solutions, the active compound content advantageously being between 0.1 to 99.9 wt %, preferably 5 to 95 wt %, more preferably 20 to 80 wt % and where, by the appropriate choice of the auxiliaries, a pharmaceutical administration form (e.g. a sustained-release form or an enteric form) exactly suited to the active compound and/or to the desired onset of action can be achieved.

The person skilled in the art is familiar on the basis of his/her expert knowledge with auxiliaries, which are suitable for the desired pharmaceutical formulations. As pharmaceutically acceptable auxiliaries, any auxiliaries known to be suitable for preparing pharmaceutical compositions can be used. Examples thereof include, but are not limited to, solvents, excipients, dispersants, emulsifiers, solubilizers, gel formers, ointment bases, antioxidants, preservatives, stabilizers, carriers, fillers, binders, thickeners, complexing agents, disintegrating agents, buffers, permeation promoters, polymers, lubricants, coating agents, propellants, tonicity adjusting agents, surfactants, colorants, flavorings, sweeteners and dyes. In particular, auxiliaries of a type appropriate to the desired formulation and the desired mode of administration are used.

Suitable oral formulations for Roflumilast and Roflumilast-N-Oxide are disclosed in the international patent application WO03/70279.

It is known to the person skilled in the art that the optimum dose of an active compound can vary as a function of the body weight, the age and the general condition of the patient, and his/her response behavior to the active compound. The optimum dose necessary in each case and manner of administration of the active compound can easily be fixed by any person skilled in the art on the basis of his expert knowledge.

In the case of oral administration of 3-cyclopropylmethoxy-4-difluoromethoxy-N-(3,5-dichloropyrid-4-yl)benzamide (Roflumilast) the daily dose (for an adult patient) is in the range from 50 to 1000 µg per day, preferably 50 to 500 µg per day, preferably by once daily administration.

In the case of intravenous administration of 3-cyclopropylmethoxy-4-difluoromethoxy-N-(3,5-dichloropyrid-4-yl)benzamide (Roflumilast) the daily dose (for an adult patient) is in the range from 50 to 500 µg per day, preferably 150 to 300 µg per day.

The compound of formula 1.1 or a pharmaceutically acceptable salt thereof and/or the compound of formula 1.2 or a pharmaceutically acceptable salt thereof may be administered together with one or more other active compounds which are used in the treatment of diabetes mellitus type 2 and/or diabetes mellitus type 1. "One or more" other active compounds in this connection means preferably 1 or 2 other active compounds.

Non-limiting examples of other active compounds which are used in the treatment of diabetes mellitus type 2 and/or type 1 are provided in the following list:

Insulin and insulin analogues
Glucagon-Like-Peptide-1 (GLP-1) receptor agonists
Sulfonylurea agents
Biguanide agents
Alpha-glucosidase inhibitors
PPAR-Agonists
Meglitinide agents
Dipeptidyl-peptidase (DPP) IV inhibitors
PDE1, PDE5, PDE9, PDE10 or PDE11 inhibitors
Amylin agonists
CoEnzym A inhibitors
Anti-obesity drugs such as appetite suppressors, satiety increasing substances, and energy expenditure increasing drugs and pharmaceutically acceptable salts thereof.

Further aspects of the present invention are therefore:

Compositions comprising an amount of the compound of formula 1.1 or a pharmaceutically acceptable salt thereof and/or the compound of formula 1.2 or a pharmaceutically acceptable salt thereof, and an amount of one or more other active compounds or pharmaceutically acceptable salts thereof which are used in the treatment of diabetes mellitus type 2 and/or type 1, wherein the first amount and the second amount together comprise an effective amount for the treatment of diabetes mellitus type 2 and/or type 1; and the above-mentioned compositions for use in the treatment of diabetes mellitus type 2 and/or type 1.

In another aspect the present invention provides the use of the compound of formula 1.1 or a pharmaceutically acceptable salt thereof and/or the compound of formula 1.2 or a pharmaceutically acceptable salt thereof in combination with one or more other active compounds or pharmaceutically acceptable salts thereof which are used in the treatment of diabetes mellitus type 2 and/or type 1 for the production of a pharmaceutical composition, combination product or kit for the treatment of diabetes mellitus type 2 and/or type 1.

The compound of formula 1.1 or a pharmaceutically acceptable salt thereof and/or the compound of formula 1.2 or a pharmaceutically acceptable salt thereof and the one or more other active compound(s) which is (are) used in the treatment of diabetes mellitus type 2 and/or diabetes mellitus type 1 can be administered simultaneously, sequentially or separately. To this effect, the active compounds of the combination can be formulated in a single formulation (pharmaceutical composition) or in separate formulations (combination product or kit).

Therefore, according to a further aspect of the present invention there is provided a pharmaceutical composition comprising a pharmaceutical formulation including an amount of a compound of formula 1.1 or a pharmaceutically acceptable salt thereof and/or a compound of formula 1.2 or a pharmaceutically acceptable salt thereof, an amount of one or more other active compounds or pharmaceutically acceptable salts thereof which are used in the treatment of diabetes mellitus type 2 and/or type 1, wherein the first amount and the second amount together comprise an effective amount for the treatment of diabetes mellitus type 2 and/or type 1, and at least one pharmaceutically acceptable auxiliary.

The above-mentioned pharmaceutical composition provides for the administration of the compound of formula 1.1 or a pharmaceutically acceptable salt thereof and/or the compound of formula 1.2 or a pharmaceutically acceptable salt thereof in admixture with one or more other active compounds or pharmaceutically acceptable salts thereof which are used in the treatment of diabetes mellitus type 2 and/or type 1 and is thus presented as a single formulation.

Alternatively, the compound of formula 1.1 or a pharmaceutically acceptable salt thereof and/or the compound of formula 1.2 or a pharmaceutically acceptable salt thereof and the one or more other active compounds or pharmaceutically acceptable salts thereof may be presented as separate formulations, wherein at least one of those formulations comprises the compound of formula 1.1 or a pharmaceutically acceptable salt thereof and/or the compound of formula 1.2 or a pharmaceutically acceptable salt thereof and at least one comprises one or more other active compounds or pharmaceutically acceptable salts thereof which are used in the treatment of diabetes mellitus type 2 and/or type 1.

Thus, there is further provided:

A combination product comprising the components: (A) an amount of the compound of formula 1.1 or a pharmaceutically acceptable salt thereof and/or the compound of formula 1.2 or a pharmaceutically acceptable salt thereof; (B) an amount of one other active compound or pharmaceutically acceptable salt thereof which is used in the treatment of diabetes mellitus type 2 and/or type 1; and optionally (C) an amount of still another active compound or pharmaceutically acceptable salt thereof which is used in the treatment of diabetes mellitus type 2 and/or type 1, wherein the first, the second and the optionally existing third amount together comprise an effective amount for the treatment of diabetes mellitus type 2 and/or type 1 and wherein each of the components (A), (B) and (C) is formulated in admixture with at least one pharmaceutically acceptable auxiliary.

A kit comprising the components: (A) a pharmaceutical formulation including an amount of the compound of formula 1.1 or a pharmaceutically acceptable salt thereof and/or the compound of formula 1.2 or a pharmaceutically acceptable salt thereof, in admixture with at least one pharmaceutically acceptable auxiliary; (B) a pharmaceutical formulation including an amount of one other active compound or pharmaceutically acceptable salt thereof which is used in the treatment of diabetes mellitus type 2 and/or type 1, in admixture with at least one pharmaceutically acceptable auxiliary; and optionally (C) a pharmaceutical formulation including an amount of still another active compound or a pharmaceutically acceptable salt thereof which is used in the treatment of diabetes mellitus type 2 and/or type 1, in admixture with at least one pharmaceutically acceptable auxiliary, wherein the first, the second and the optionally existing third amount together comprise an effective amount for the treatment of diabetes mellitus type 2 and/or type 1.

Simultaneous administration of the compound of formula 1.1 or a pharmaceutically acceptable salt thereof and/or the compound of formula 1.2 or a pharmaceutically acceptable salt thereof and one or more other active compounds or pharmaceutically acceptable salts thereof which are used in the treatment of diabetes mellitus type 2 and/or type 1 can be accomplished, by administering to the patient in need of diabetes mellitus type 2 and/or type 1 therapy the pharmaceutical composition according to the invention in one dosage form, such as for example in a single capsule, tablet or injection.

Components (A), (B) and the optionally existing component (C) of the combination product as well as of the kit may be administered sequentially or separately over the course of the treatment of diabetes mellitus type 2 and/or type 1.

Sequential or separate administration of the compound of formula 1.1 or a pharmaceutically acceptable salt thereof and/or the compound of formula 1.2 or a pharmaceutically acceptable salt thereof and one or more other active compounds or pharmaceutically acceptable derivatives thereof which are used in the treatment of diabetes mellitus type 2 and/or type 1 can be accomplished, by administering to the patient in need of diabetes mellitus type 2 and/or type 1 therapy components (A), (B) and the optionally existing component (C) of the combination product or the kit according to the invention in (multiple) separate dosage forms, such as for example, in separate capsules, tablets or injections.

In an alternative, one or two of the components (A), (B) and the optionally existing component (C) may be formulated as tablet or capsule and the other component(s) may be formulated for administration, for example, by injection or inhalation.

Sequential administration encompasses a short period between the administration of components (A), (B) and the optionally existing component (C) of the combination product or the kit according to the invention (for example, the time that is needed to swallow one tablet after the other).

Separate administration encompasses both relatively short and relatively long periods between the administration of components (A), (B) and the optional existing component (C) of the combination product or the kit of parts according to the invention. However, for the purposes of the present invention at least one of the components is administered while the other component(s) is (are) still having an effect on the patient being treated. In a preferred embodiment of the invention the effect on the subject being treated is a synergistic effect.

The combined administration of the compound of formula 1.1 or a pharmaceutically acceptable salt thereof and/or the compound of formula 1.2 or a pharmaceutically acceptable salt thereof and one or more other active compounds or pharmaceutically acceptable salts thereof which are used in the treatment of diabetes mellitus type 2 and/or type 1, either in form of the pharmaceutical composition, combination product or kit according to the invention, lead to an effective treatment for diabetes mellitus type 2 and/or type 1, and in a preferred embodiment is superior to the use of either agent alone. Moreover, in a particularly preferred embodiment, the combined administration of the compound of formula 1.1 or a pharmaceutically acceptable salt thereof and/or the compound of formula 1.2 or a pharmaceutically acceptable salt thereof and one or more other active compounds or pharmaceutically acceptable salts thereof which are used in the treatment of diabetes mellitus type 2 and/or type 1 shows a synergistic efficacy for treating diabetes mellitus type 2 and/or type 1.

As used herein, the term "synergistic" refers to the combination of the compound of formula 1.1 or a pharmaceutically acceptable salt thereof and/or the compound of formula 1.2 or a pharmaceutically acceptable salt thereof with one or more other active compounds or pharmaceutically acceptable salts thereof which are used in the treatment of diabetes mellitus type 2 and/or type 1 either in form of the pharmaceutical composition, combination product or kit according to the invention having an efficacy for the treatment of diabetes mellitus type 2 and/or type 1 that is greater than would be expected from the sum of their individuals effects. The synergistic effects of the embodiments of the present invention encompass additional unexpected advantages for the treatment of diabetes mellitus type 2 and/or type 1. Such additional advantages may include, but are not limited to, lowering the required dose of one or more of the active compounds of the combination, reducing the side effects of one or more of the active compounds of the combination or rendering one or more of the active compounds more tolerable to the patient in need of diabetes mellitus type 2 and/or type 1 therapy.

The combined administration of the compound of formula 1.1 or a pharmaceutically acceptable salt thereof and/or the compound of formula 1.2 or a pharmaceutically acceptable salt thereof and one or more other active compounds or pharmaceutically acceptable derivatives thereof which are used in the treatment of diabetes mellitus type 2 and/or type 1 may also be useful for decreasing the required number of separate dosages, thus, potentially improving compliance of the patient in need of diabetes mellitus type 2 and/or type 1 therapy.

A further aspect of the present invention is the use of a pharmaceutical composition, a pharmaceutical combination or a kit according to the invention for the production of a medicament for the treatment of diabetes mellitus type 2 and/or type 1.

Still a further aspect of the present invention is a method for treating diabetes mellitus type 2 and/or type 1 comprising administering to a patient in need thereof a pharmaceutical composition comprising a pharmaceutical formulation including an amount of a compound of formula 1.1 or a pharmaceutically acceptable salt thereof and/or a compound of formula 1.2 or a pharmaceutically acceptable salt thereof, an amount of one or more other active compound(s) or a pharmaceutically acceptable salt(s) thereof which is (are) used in the treatment of diabetes mellitus type 2 and/or type 1, wherein the first amount and the second amount together comprise an effective amount for the treatment of diabetes mellitus type 2 and/or type 1, and at least one pharmaceutically acceptable auxiliary.

Another aspect of the present invention is a method for treating diabetes mellitus type 2 and/or type 1 comprising administering to a patient in need thereof a combination product comprising the components:
(A) an amount of the compound of formula 1.1 or a pharmaceutically acceptable salt thereof and/or the compound of formula 1.2 or a pharmaceutically acceptable salt thereof;
(B) an amount of one other active compound or a pharmaceutically acceptable salt thereof which is used in the treatment of diabetes mellitus type 2 and/or type 1; and optionally
(C) an amount of a further active compound or a pharmaceutically acceptable salt thereof which is used in the treatment of diabetes mellitus type 2 and/or type 1,
wherein the first, the second and the optionally existing third amount together comprise an effective amount for the treatment of diabetes mellitus type 2 and/or type 1;
wherein each of the components (A), (B) and the optionally existing component (C) is formulated in admixture with at least one pharmaceutically acceptable auxiliary;
and wherein the components (A), (B) and the optionally existing component (C) are administered sequentially or separately.

As already mentioned above examples of other anti-diabetic compounds useful in the pharmaceutical compositions, combination products and kits according to the invention are selected from the group consisting of:
Insulin and insulin analogues
Glucagon-Like-Peptide-1 (GLP-1) receptor agonists
Sulfonylurea agents
Biguanide agents
Alpha-glucosidase inhibitors
PPAR-Agonists
Meglitinide agents
Dipeptidyl-peptidase (DPP) IV inhibitors
PDE1, PDE5, PDE9, PDE10 or PDE11 inhibitors
Amylin agonists
CoEnzym A inhibitors
Anti-obesity drugs such as appetite suppressors, satiety increasing substances, and energy expenditure increasing drugs
and pharmaceutically acceptable salts thereof.

In one embodiment of the invention, the other active compound(s) which is (are) used in the treatment of diabetes mellitus type 2 and/or type 1 is (are) selected from the group consisting of
Insulin and insulin analogues
Glucagon-Like-Peptide-1 (GLP-1) receptor agonists
Sulfonylurea agents
Biguanide agents
Alpha-glucosidase inhibitors
PPAR-Agonists
Meglitinide agents
Dipeptidyl-peptidase (DPP) IV inhibitors
PDE1, PDE5, PDE9, PDE10 or PDE11 inhibitors
Amylin agonists
CoEnzym A inhibitors
Anti-obesity drugs such as appetite suppressors, satiety increasing substances, and energy expenditure increasing drugs
and pharmaceutically acceptable salts thereof.

In another embodiment of the present invention the other active compound which is used in the treatment of diabetes mellitus type 2 and/or type 1 is insulin. Specific examples of insulin include, but are not limited to Humulin® [human insulin, (rDNA origin)], Novolin® [human insulin, (rDNA origin)], Velosulin® BR [human buffered regular insulin, (rDNA origin)] and Exubera® [human insulin, inhaled].

In another embodiment of the present invention the other active compound which is used in the treatment of diabetes mellitus type 2 and/or type 1 is an insulin analogue or a pharmaceutically acceptable salt thereof. Specific examples of insulin analogues include, but are not limited to, novarapid, insulin detemir, insulin lispro, insulin glargine, insulin zinc suspension and Lys-Pro insulin.

In another embodiment of the present invention the other active compound which is used in the treatment of diabetes mellitus type 2 and/or type 1 is a Glucagon-Like-Peptide-1 receptor agonist or a pharmaceutically acceptable salt thereof. Specific examples of Glucagon-Like-Peptide-1 receptor agonists include, but are not limited to BIM-51077 (CAS-No. 275371-94-3), EXENATIDE (CAS-No. 141758-74-9), CJC-1131 (CAS-No. 532951-64-7), LIRAGLUTIDE (CAS-No. 20656-20-2) and ZP-10 (CAS-No. 320367-13-3). A preferred Glucagon-Like-Peptide-1 receptor agonist is EXENATIDE.

In another embodiment of the present invention the other active compound which is used in the treatment of diabetes mellitus type 2 and/or type 1 is a sulfonylurea agent or a pharmaceutically acceptable salt thereof. Specific examples of sulfonylurea agents include, but are not limited to, TOLBUTAMIDE (CAS-No. 000064-77-7), TOLAZAMIDE (CAS-No. 001156-19-0), GLIPIZIDE (CAS-No. 029094-61-9), CARBUTAMIDE (CAS-No. 000339-43-5), GLISOXEPIDE (CAS-No. 025046-79-1), GLISENTIDE (CAS-No. 032797-92-5), GLIBORNURIDE (CAS-No. 026944-48-9), GLIBENCLAMIDE (CAS-NO. 010238-21-8), GLIQUIDONE (CAS-No. 033342-05-1), GLIMEPIRIDE (CAS-No. 093479-97-1) and GLICLAZIDE (CAS-No. 021187-98-4).

In another embodiment of the present invention the pharmaceutically acceptable salt of TOLBUTAMIDE is the sodium salt of TOLBUTAMIDE. In another embodiment of the present invention the pharmaceutically acceptable salt of GLIQUIDONE is the sodium salt of GLIQUIDONE.

In another embodiment of the present invention the other active compound which is used in the treatment of diabetes mellitus type 2 and/or type 1 is a biguanide agent or a pharmaceutically acceptable salt thereof. A specific example of a biguanide agent includes, but is not limited to METFORMIN (CAS-No. 000657-24-9).

In another embodiment of the present invention the pharmaceutically acceptable salt of METFORMIN is the monohydrochloride salt of METFORMIN.

In another embodiment of the present invention the other active compound which is used in the treatment of diabetes mellitus type 2 and/or type 1 is an alpha-glucosidase-inhibitor or a pharmaceutically acceptable salt thereof. Specific examples of alpha-glucosidase-inhibitors include, but are not limited to ACARBOSE (Cas-No. 056180-94-0), MIGLITOL (CAS-No. 072432-03-2) and VOGLIBOSE (CAS-No. 083480-29-9).

In another embodiment of the present invention the other active compound which is used in the treatment of diabetes mellitus type 2 and/or type 1 is a PPAR-agonist or a pharmaceutically acceptable salt thereof. Specific examples of PPAR-agonists include, but are not limited to MURAGLITAZAR (CAS-No. 331741-94-7), ROSIGLITAZONE (CAS-NO. 122320-73-4), PIOGLITAZONE (CAS-No. 111025-46-8), RA-GAGLITAZAR (CAS-No. 222834-30-2), FARGLITAZAR (CAS-No. 196808-45-4), TESAGLITAZAR (CAS-No. 251565-85-2), NAVEGLITAZAR (CAS-No. 476436-68-7), NETOGLITAZONE (CAS-NO. 161600-01-7), RIVOGLITAZONE (CAS-No. 185428-18-6), K-111 (CAS-No. 221564-97-2), GW-677954 (CAS-No. 622402-24-8), FK-614 (CAS-No 193012-35-0) and (–)-Halofenate (CAS-No. 024136-23-0). Preferred PPAR-agonists are ROSGLITAZONE and PIOGLITAZONE.

In another embodiment of the present invention the pharmaceutically acceptable salt of ROSIGLITAZONE is the maleate salt of ROSIGLITAZONE. In another embodiment of the present invention the pharmaceutically acceptable salt of RIVOGLITAZONE is the mono-hydrochloride salt of RIVOGLITAZONE. In another embodiment of the present invention the pharmaceutically acceptable salt of K-111 is the sodium salt of K-111. In another embodiment of the present invention the pharmaceutically acceptable salt of PIOGLITAZONE is the dihydrochloride salt of PIOGLITAZONE.

In another embodiment of the present invention the other active compound which is used in the treatment of diabetes mellitus type 2 and/or type 1 is a meglitinide agent or a pharmaceutically acceptable salt thereof. Specific examples of meglitinide agents include, but are not limited to REPAGLINIDE (CAS-No. 135062-02-1), NATEGLINIDE (CAS-No. 105816-04-4) and MITIGLINIDE (CAS-No. 145375-43-5).

In another embodiment of the present invention the pharmaceutically acceptable salts of MITIGLINIDE are the monopotassium or the calcium salt of MITIGLINIDE.

In another embodiment of the present invention the other active compound which is used in the treatment of diabetes mellitus type 2 and/or type 1 is a DPP-IV inhibitor or a pharmaceutically acceptable salt thereof. Specific examples of DPP IV inhibitors include, but are not limited to SITAGLIPTIN (CAS-No. 486460-32-6), SAXAGLIPTIN (CAS-No. 361442-04-8), VILDAGLIPTIN (CAS-No. 274901-16-5), DENAGLIPTIN (CAS-No. 483369-58-0), P32/98 (CAS-No. 251572-70-0) and NVP-DPP-728 (CAS-No. 247016-69-9).

In another embodiment of the present invention the pharmaceutically acceptable salt of SITAGLIPTIN is the phosphate salt of SITAGLIPTIN. In another embodiment of the present invention the pharmaceutically acceptable salts of P32/98 are the fumarate or hydrochloride salt of P32/98.

In another embodiment of the present invention the other active compound which is used in the treatment of diabetes mellitus type 2 and/or type 1 is a PDE5 inhibitor or a pharmaceutically acceptable salt thereof. Specific examples of PDE5 inhibitors include, but are not limited to SILDENAFIL (CAS-No. 139755-83-2), VARDENAFIL (CAS-No. 224785-90-4) and TADALAFIL (CAS-No. 171596-29-5).

In another embodiment of the present invention the pharmaceutically acceptable salts of SILDENAFIL are the hemicitrate, the citrate or the mesilate salt of SILDENAFIL; particularly preferred is the citrate salt of SILDENAFIL. In another embodiment of the present invention the pharmaceutically acceptable salts of VARDENAFIL are the mono-hydrochloride salt of VARDENAFIL or the dihydrochloride salt of VARDENAFIL.

In another embodiment of the present invention the other active compound which is used in the treatment of diabetes mellitus type 2 and/or type 1 is a PDE1, PDE9, PDE10 or PDE11 inhibitor or a pharmaceutically acceptable salt thereof. PDE1, PDE9, PDE10 or PDE11 inhibitors which may be useful employed according to the present invention, can be found, for example, in US20020160939, WO2003037432, US2004220186, WO2005/003129, WO2005012485, WO2005120514 and WO03077949.

In another embodiment of the present invention the other active compound which is used in the treatment of diabetes mellitus type 2 and/or type 1 is a amylin agonist or a pharmaceutically acceptable salt thereof. A specific example of a amylin agonist includes, but is not limited to PRAMLINITIDE (CAS-No. 151126-32-8)

In another embodiment of the present invention the pharmaceutically acceptable salt of PRAMLINITIDE is the acetate salt of PRAMLINITIDE.

In another embodiment of the present invention the other active compound which is used in the treatment of diabetes mellitus type 2 and/or type 1 is a Coenzyme A inhibitor or a pharmaceutically acceptable salt thereof. A specific example of a Coenzyme A inhibitor includes, but is not limited to ETOMOXIR (CAS-No. 082258-36-4).

In another embodiment of the present invention the other active compound which is used in the treatment of diabetes mellitus type 2 and/or type 1 is an anti-obesity drug or a pharmaceutically acceptable salt thereof. Specific examples of anti-obesity drugs include, but are not limited to HMR-1426 (CAS-No. 262376-75-0), CETILISTAT (CAS-No. 282526-98-1) and SIBUTRAMINE (CAS-No. 106650-56-0).

In another embodiment of the present invention the pharmaceutically acceptable salt of HMR-1426 is the hydrochloride salt of HMR-1426. In another embodiment of the present invention the pharmaceutically acceptable salt of SIBUTRAMINE is the hydrochloride salt of SIBUTRAMINE.

More details with respect to preferred combination partners for the compounds of formula 1.1 and/or formula 1.2 are listed in Table 1:

TABLE 1

| INN or Research Code | Structure/Chemical Name |
|---|---|
| BIM-51077 | L-histidyl-2-methylalanyl-L-glutamyl-glycyl-L-threonyl-L-phenylalanyl-L-threonyl-L-seryl-L-aspartyl-L-valyl-L-seryl-L-seryl-L-tyrosyl-L-leucyl-L-glutamyl-glycyl-L-glutaminyl-L-alanyl-L-alanyl-L-lysyl-L-glutamyl-L-phenylalanyl-L-isoleucyl-L-alanyl-L-tryptophyl-L-leucyl-L-valyl-L-lysyl-2-methylalanyl-L-argininamide |
| EXENATIDE | L-histidylglycyl-L-glutamylglycyl-L-threonyl-L-phenylalanyl-L-threonyl-L-seryl-L-aspartyl-L-leucyl-L-seryl-L-lysyl-glutaminyl-L-methionyl-L-glutamyl-L-glutamyl-L-glutamyl-L-alanyl-Lvalyl-L-arginyl-L-leuycl-L-phenylalanyl-L-isoleucyl-L-glutamyl-L-tryptophyl-L-leucyl-L-lysyl-L-asparaginylglyclglycyl-L-prolyl-L-seryl-L-serylglycyl-L-alanyl-L-prolyl-L-prolyl-L-prolyl-L-serinamide |
| CJC-1131 | L-histidyl-D-alanyl-L-alpha-glutamylglycyl-L-threonyl-L-phenylalanyl-L-threonyl-L-seryl-L-alpha-aspartyl-L-valyl-L-seryl-L-seryl-L-tyrosyl-L-leucyl-L-alpha-glutamylglycyl-L-glutaminyl-L-alanyl-L-alanyl-L-lysyl-L-alpha-glutamyl-L-phenylalanyl-L-isoleucyl-L-alanyl-L-tryptophyl-L-leucyl-L-valyl-L-lysylglycyl-L-arginyl-N6-[2-[2-[2-[3-(2,5-dioxo-2,5-dihydro-1H-pyrrol-1-yl)propionamido]ethoxy]ethoxy]acetyl]-L-lysin-amide |
| LIRAGLUTIDE | L-histidyl-L-alanyl-L-glutamyl-glycyl-L-threonyl-L-phenylalanyl-L-threonyl-L-seryl-L-aspartyl-L-valyl-L-seryl-L-seryl-L-tyrosyl-L-leucyl-L-glutamyl-glycyl-L-glutaminyl-L-alanyl-L-alanyl-Nepsilon-(Nalpha-hexadecanoyl-gamma-L-glutamyl)-L-lysyl-L-glutamyl-L-phenylalanyl-L-isoleucyl-L-alanyl-L-tryptophyl-L-leucyl-L-valyl-L-arginyl-glycyl-L-arginyl-glycine |
| ZP-10 | H-His-Gly-Glu-Gly-Thr-Phe-Thr-Ser-Asp-Leu-Ser-Lys-Gln-Met-Glu-Glu-Glu-Ala-Val-Arg-Leu-Phe-Ile-Glu-Trp-Leu-Lys-Asn-Gly-Gly-Pro-Ser-Ser-Gly-Ala-Pro-Pro-Ser-Lys-Lys-Lys-Lys-Lys-Lys-NH2 |
| TOLBUTAMIDE | 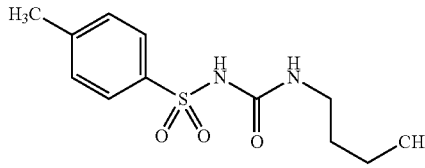

N-[(butylamino)carbonyl]-4-methylbenzenesulfonamide |
| TOLAZAMIDE | 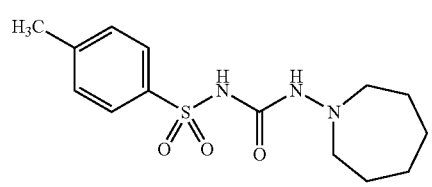

N-[(azepan-1-ylamino)carbonyl]-4-methyl-benzenesulfonamide |
| GLIPIZIDE | 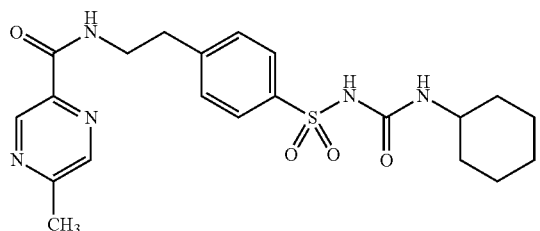

N-{2-[4-({[(cyclohexylamino)carbonyl]amino}sulfonyl)phenyl]ethyl}-5-methylpyrazine-2-carboxamide |

TABLE 1-continued

| INN or Research Code | Structure/Chemical Name |
| --- | --- |
| CARBUTAMIDE | 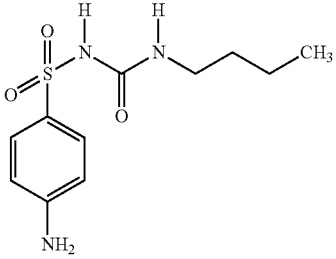<br>4-amino-N-[(butylamino)carbonyl]benzenesulfonamide |
| GLISOXEPIDE | 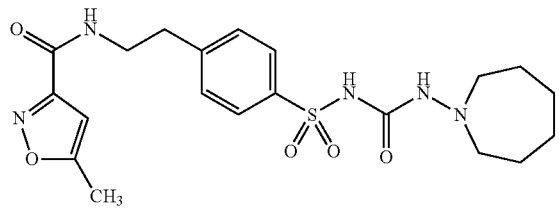<br>N-{2-[4-({[(azepan-1-ylamino)carbonyl]amino}sulfonyl)phenyl]ethyl}-5-methylisoxazole-3-carboxamide |
| GLISENTIDE | 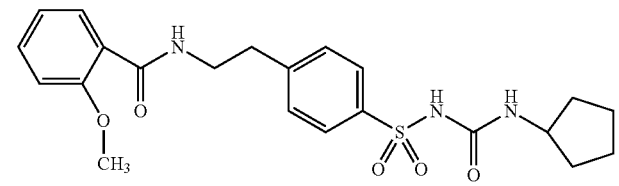<br>N-{2-[4-({[(cyclopentylamino)carbonyl]amino}sulfonyl)phenyl]ethyl}-2-methoxybenzamide |
| GLIBORNURIDE | 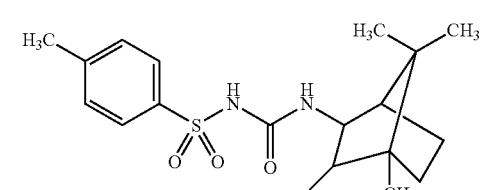<br>N-{[(3-hydroxy-4,7,7-trimethylbicyclo[2.2.1]hept-2-yl)amino]carbonyl}-4-methylbenzenesulfonamide |
| GLIBENCLAMIDE | 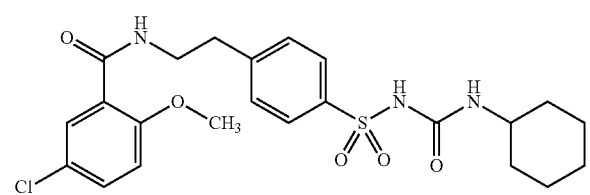<br>5-chloro-N-{2-[4-({[(cyclohexylamino)carbonyl]amino}sulfonyl)phenyl]ethyl}-2-methoxybenzamide |

TABLE 1-continued

| INN or Research Code | Structure/Chemical Name |
|---|---|
| GLIQUIDONE | N-[(cyclohexylamino)carbonyl]-4-[2-(7-methoxy-4,4-dimethyl-1,3-dioxo-3,4-dihydroisoquinolin-2(1H)-yl)ethyl]benzenesulfonamide |
| GLIMEPIRIDE | 3-ethyl-4-methyl-N-(2-{4-[({[(trans-4-methylcyclohexyl)amino]carbonyl}amino)sulfonyl]phenyl}ethyl)-2-oxo-2,5-dihydro-1H-pyrrole-1-carboxamide |
| GLICLAZIDE | N-[(hexahydrocyclopenta[c]pyrrol-2(1H)-ylamino)carbonyl]-4-methylbenzenesulfonamide |
| METFORMIN | N,N-dimethylimidodicarbonimidic diamide |
| ACARBOSE | 4,6-dideoxy-4-{[4,5,6-trihydroxy-3-(hydroxymethyl)cyclohex-2-en-1-yl]amino}hexopyranosyl-(1→4)hexopyranosyl-(1→4)hexopyranose |

TABLE 1-continued

| INN or Research Code | Structure/Chemical Name |
|---|---|
| MIGLITOL | 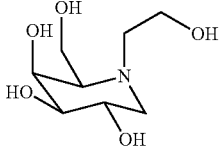<br>1-(2-hydroxyethyl)-2-(hydroxymethyl)piperidine-3,4,5-triol |
| VOGLIBOSE | 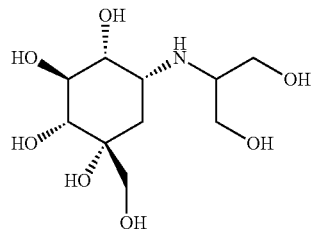<br>(1R,2R,3S,4R,5R)-5-{[2-hydroxy-1-(hydroxymethyl)ethyl]amino}-1-(hydroxymethyl)cyclohexane-1,2,3,4-tetrol |
| MURAGLITAZAR | 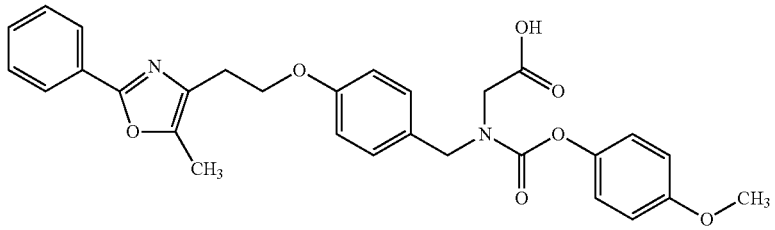<br>N-[(4-methoxyphenoxy)carbonyl]-N-{4-[2-(5-methyl-2-phenyl-1,3-oxazol-4-yl)ethoxy]benzyl}glycine |
| ROSIGLITAZONE | 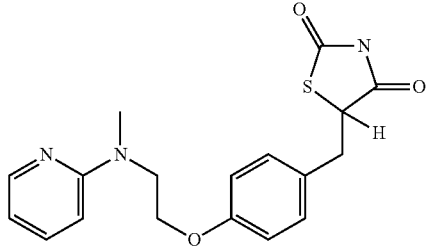<br>(5RS)-5-(4-{2-[methyl(pyridin-2-yl)amino]ethoxy}benzyl)-1,3-thiazolidine-2,4-dione |
| PIOGLITAZONE | 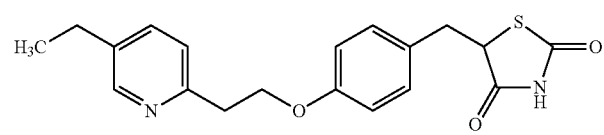<br>5-{4-[2-(5-ethylpyridin-2-yl)ethoxy]benzyl}-1,3-thiazolidine-2,4-dione |

TABLE 1-continued

| INN or Research Code | Structure/Chemical Name |
|---|---|
| RAGAGLITAZAR | 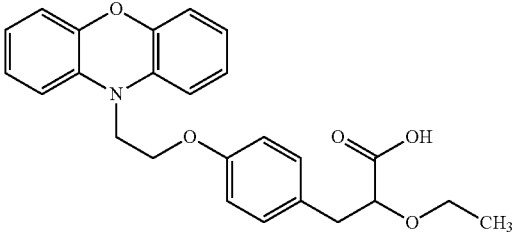<br>2-ethoxy-3-{4-[2-(10H-phenoxazin-10-yl)ethoxy]phenyl} propanoic acid |
| FARGLITAZAR | 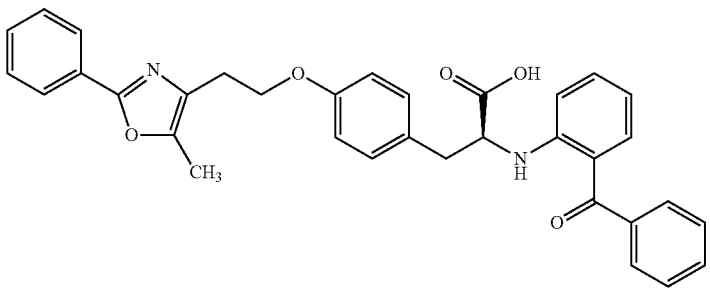<br>N-(2-benzoylphenyl)-O-[2-(5-methyl-2-phenyl-1,3-oxazol-4-yl)ethyl]-L-tyrosine |
| TESAGLITAZAR | 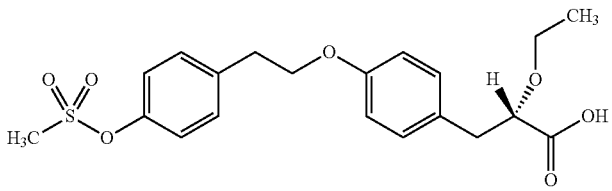<br>(2S)-2-ethoxy-3-[4-(2-{4-[(methylsulfonyl)oxy]phenyl}ethoxy)phenyl]propanoic acid |
| NAVEGLITAZAR | 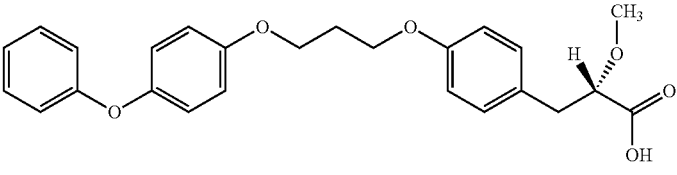<br>(2S)-2-methoxy-3-{4-[3-(4-phenoxyphenoxy)propoxy]phenyl}propanoic acid |
| NETOGLITAZONE | 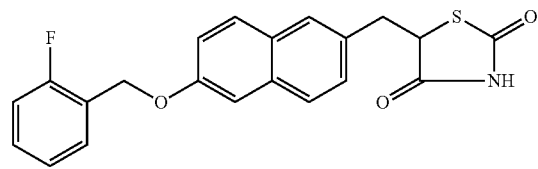<br>5-({6-[(2-fluorobenzyl)oxy]-2-naphthyl}methyl)-1,3-thiazolidine-2,4-dione |

TABLE 1-continued

| INN or Research Code | Structure/Chemical Name |
|---|---|
| RIVOGLITAZONE | 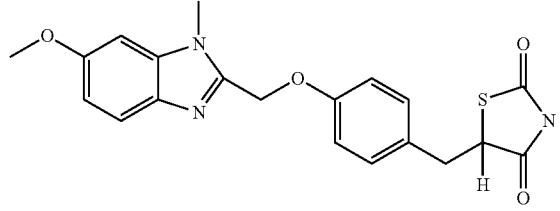<br>(5R)-5-{4-[(6-methoxy-1-methyl-1H-benzimidazol-2-yl)methoxy]benzyl}-1,3-thiazolidine-2,4-dione |
| K-111 | 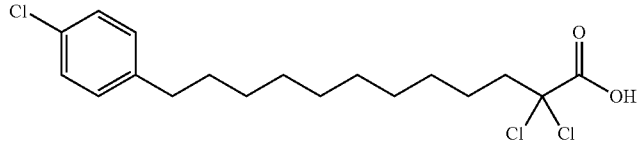<br>2,2-dichloro-12-(4-chlorophenyl)dodecanoic acid |
| GW-677954 | 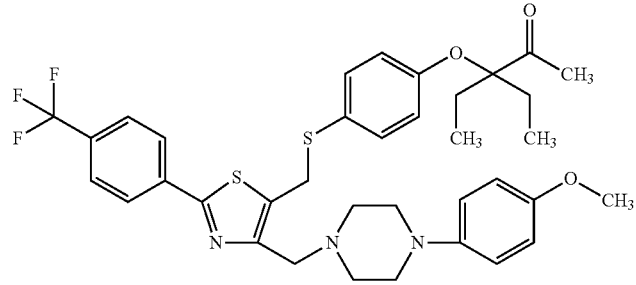<br>2-ethyl-2-(4-{[(4-{[4-(4-methoxyphenyl)piperazin-1-yl]methyl}-2-[4-(trifluoromethyl)phenyl]-1,3-thiazol-5-yl)methyl]thio}phenoxy)butanoic acid |
| FK-614 | 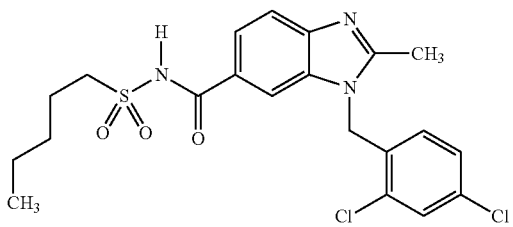<br>1-(2,4-dichlorobenzyl)-2-methyl-N-(pentylsulfonyl)-1H-benzimidazole-6-carboxamide |
| (−)-Halofenate | 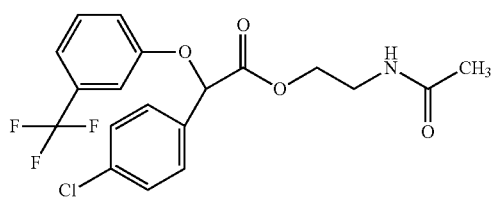<br>(−)-2-Acetamidoethyl 4-chlorophenyl(3-trifluoromethylphenoxy)acetate |

TABLE 1-continued

| INN or Research Code | Structure/Chemical Name |
|---|---|
| REPAGLINIDE | 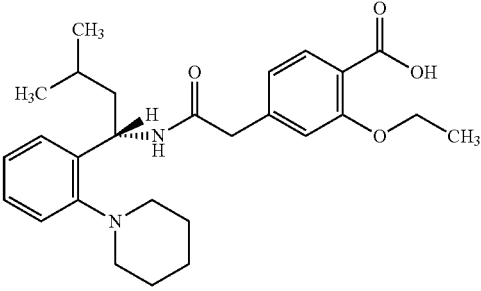<br>2-ethoxy-4-(2-{[(1S)-3-methyl-1-(2-piperidin-1-ylphenyl)butyl]amino}-2-oxoethyl)benzoic acid |
| NATEGLINIDE | 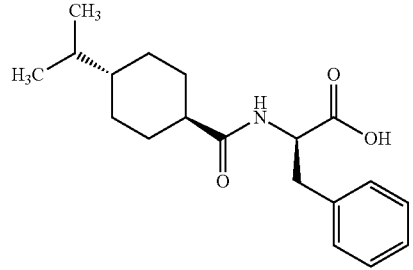<br>N-[(trans-4-isopropylcyclohexyl)carbonyl]-D-phenylalanine |
| MITIGLINIDE | 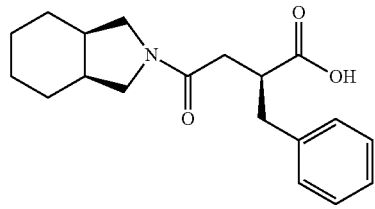<br>(2S)-2-benzyl-4-[(3aR,7aS)-octahydro-2H-isoindol-2-yl]-4-oxobutanoic acid |
| SITAGLIPTIN | 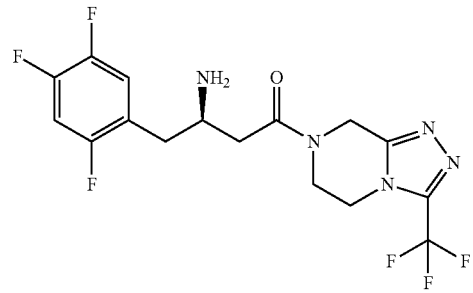<br>(2R)-4-oxo-4-[3-(trifluoromethyl)-5,6-dihydro[1,2,4]triazolo[4,3-a]pyrazin-7(8H)-yl]-1-(2,4,5-trifluorophenyl)butan-2-amine |

TABLE 1-continued

| INN or Research Code | Structure/Chemical Name |
|---|---|
| SAXAGLIPTIN | 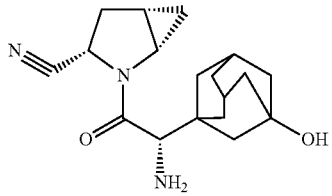<br>(1S,3S,5S)-2-[(2S)-2-amino-2-(3-hydroxy-1-adamantyl)acetyl]-2-azabicyclo[3.1.0]hexane-3-carbonitrile |
| VILDAGLIPTIN | 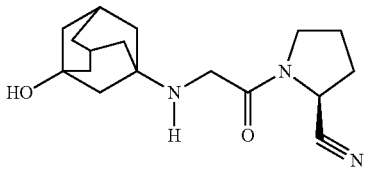<br>(2S)-1-[N-(3-hydroxy-1-adamantyl)glycyl]pyrrolidine-2-carbonitrile |
| DENAGLIPTIN | 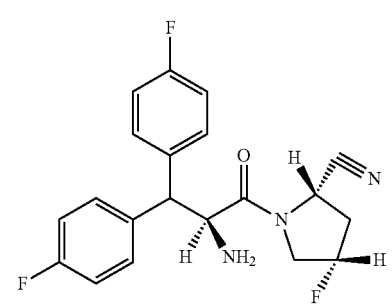<br>(2S,4S)-4-fluoro-1-[4-fluoro-β-(4-fluorophenyl)-L-phenylalanyl]pyrrolidine-2-carbonitrile |
| P32/98 | 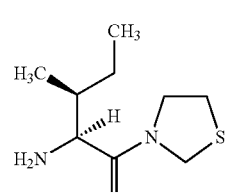<br>(2S,3S)-3-methyl-1-oxo-(1,3-thiazolidin-3-yl)pentan-2-amine |
| NVP-DPP-728 | 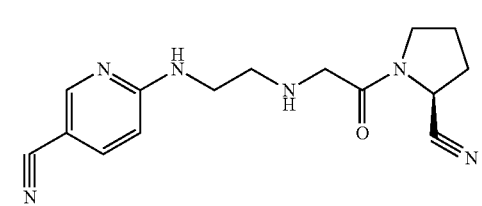<br>6-{[2-({2-[(2S)-2-cyanopyrrolidin-1-yl]-2-oxoethyl}amino)ethyl]amino}nicotinonitrile |

TABLE 1-continued

| INN or Research Code | Structure/Chemical Name |
|---|---|
| SILDENAFIL | 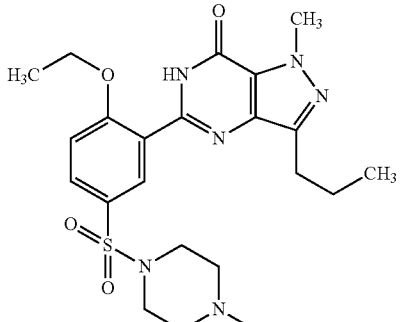<br>5-{2-ethoxy-5-[(4-methylpiperazin-1-yl)sulfonyl]phenyl}-1-methyl-3-propyl-1,6-dihydro-7H-pyrazole[4,3-d]pyrimidin-7-one |
| VARDENAFIL | 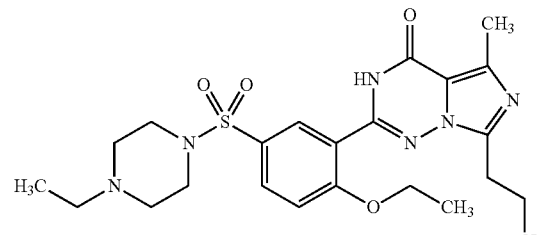<br>2-{2-ethoxy-5-[(4-ethylpiperazin-1-yl)sulfonyl]phenyl}-5-methyl-7-propylimidazo[5,1-f][1,2,4]triazin-4(3H)-one |
| TADALAFIL | 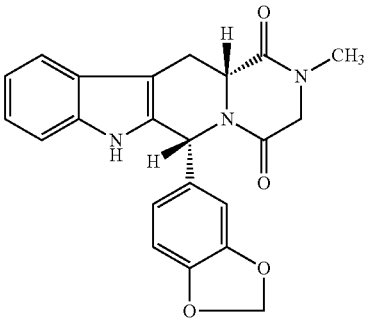<br>(6R,12aR)-6-(1,3-benzodioxol-5-yl)-2-methyl-2,3,6,7,12,12a-hexahydropyrazino[1',2':1,6]pyrido[3,4-b]indole-1,4-dione |
| PRAMLINTIDE | L-lysyl-L-cysteinyl-L-asparaginyl-L-threonyl-L-alanyl-L-threonyl-L-cysteinyl-L-alanyl-L-threonyl-L-glutaminyl-L-arginyl-L-leucyl-L-alanyl-L-asparaginyl-L-phenylalanyl-L-leucyl-L-valyl-L-histidyl-L-seryl-L-seryl-L-asparaginyl-L-asparaginyl-L-phenylalanylglycyl-L-prolyl-L-isoleucyl-L-leucyl-L-prolyl-L-prolyl-L-threonyl-L-asparaginyl-L-valylglycyl-L-seryl-L-asparaginyl-L-threonyl-L-tyrosinamide, cyclic (2->7)disulfide |

TABLE 1-continued

| INN or Research Code | Structure/Chemical Name |
|---|---|
| ETOMOXIR | 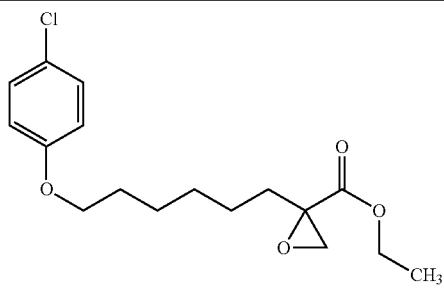<br>ethyl 2-[6-(4-chlorophenoxy)hexyl]oxirane-2-carboxylate |
| HMR-1426 | 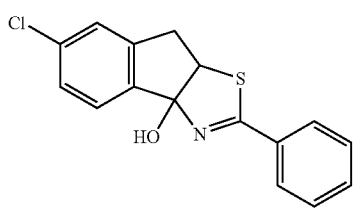<br>6-chloro-2-phenyl-8,8a-dihydro-3aH-indeno[1,2-d][1,3]thiazol-3a-ol |
| CETILISTAT | 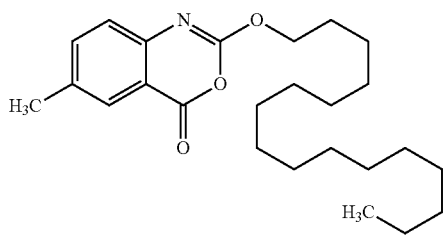<br>2-(hexadecyloxy)-6-methyl-4H-3,1-benzoxazin-4-one |
| SIBUTRAMINE | 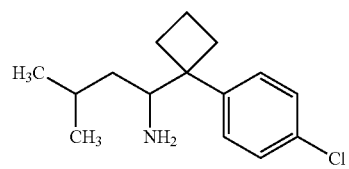<br>1-[1-(4-chlorophenyl)cyclobutyl]-3-methylbutan-1-amine |

Additional information with regard to the preparation, suitable dosage forms and dose ranges of the glucagon-like-peptide-1 receptor agonists listed in Table 1 can be found in the following patents/patent applications: WO0334331, EP0981611, EP1180121, WO9808871 and WO0104156.

The sulfonylurea agents TOLBUTAMIDE, TOLAZAMIDE, GLIPIZIDE, CARBUTAMIDE, GLISOXEPIDE; GLISENTIDE, GLIBORNURIDE, GLIBENCLAMIDE, GLIQUIDONE, GLIMEPIRIDE and GLICLAZIDE listed in Table 1 are commercially available. The person skilled in the art is familiar with suitable formulations and dose ranges of these compounds.

The biguanide agent METFORMIN listed in Table 1 is commercially available. The person skilled in the art is familiar with suitable formulations and dose ranges of this compound.

The alpha-glucosidase inhibitors ACARBOSE, MIGLITOL and VOGLIBOSE listed in Table 1 are commercially available. The person skilled in the art is familiar with suitable formulations and dose ranges of this compound.

Additional information with regard to the preparation, suitable dosage forms and dose ranges of the PPAR-agonists listed in Table 1 can be found in the following patents/patent applications: WO0121602, EP03306228, EP0658161, EP0193256, WO9919313, WO9731907, WO9962870, WO0140169, WO02100813, EP0604983, EP0745600, WO9615784, WO0259098, EP0882718 and EP1183020.

The metiglinide agents REPAGLINIDE, NATEGLINIDE and MITIGLINIDE listed in Table 1 are commercially available. The person skilled in the art is familiar with suitable formulations and dose ranges of this compound.

Additional information with regard to the preparation, suitable dosage forms and dose ranges of the DPP IV inhibitors listed in Table 1 can be found in the following patents/patent applications: WO03004498, WO0168603, WO0034241, WO0302531, WO9961431 and WO9919998.

Additional information with regard to the preparation, suitable dosage forms and dose ranges of the PDE5 inhibitors listed in Table 1 can be found in the following patents/patent applications: WO0213798, WO0260422 and WO2004082667.

Additional information with regard to the preparation, suitable dosage forms and dose ranges of the amylin analogue PRAMLINTIDE listed in Table 1 can be found in EP0567626.

Additional information with regard to the preparation, suitable dosage forms and dose ranges of ETOXOMIR, HMR-1426, CETILISTAT and SIBUTRAMINE listed in Table 1 can be found in the following patents/patent applications: EP0046590, WO0018749, EP1144395 and EP0397831.

"Pharmaceutically acceptable salts" of the other active compound(s) which is (are) used in the treatment of diabetes mellitus type 2 and/or type 1 are not limited to the specific examples given above. The term refers to non-toxic salts of these compounds. These pharmaceutically acceptable salts are generally prepared by reacting a free base with a suitable organic or inorganic acid or by reacting an acid with a suitable organic or inorganic base. Particular mention may be made of the pharmaceutically acceptable inorganic and organic acids customarily used in pharmacy. Those suitable are in particular water-soluble and water-insoluble acid addition salts with acids such as, for example, hydrochloric acid, hydrobromic acid, phosphoric acid, nitric acid, sulfuric acid, acetic acid, citric acid, D-gluconic acid, benzoic acid, 2-(4-hydroxybenzoyl)-benzoic acid, butyric acid, sulfosalicylic acid, maleic acid, lauric acid, malic acid, fumaric acid, succinic acid, oxalic acid, tartaric acid, embonic acid, stearic acid, toluenesulfonic acid, methanesulfonic acid or 1-hydroxy-2-naphthoic acid. As examples of pharmaceutically acceptable salts with bases may be mentioned the lithium, sodium, potassium, calcium, aluminium, magnesium, titanium, ammonium, meglumine or guanidinium salts.

It is understood that the other active compound(s) which is (are) used in the treatment of diabetes mellitus type 2 and/or type 1 and their pharmaceutically acceptable salts can also be present in the form of their pharmaceutically acceptable solvates, and in particular in the form of their hydrates.

Mode of administration, dosage forms and dosage of the combinations:

The combinations according to the invention may be administered by any suitable route, for example, by the oral, sublingual, buccal, intravenous, intraarterial, intramuscular, subcutaneous, intracutaneous, topical, transdermal, intranasal, intraperitoneal, rectal or vaginal route, by inhalation or by insufflation.

Tablets, coated tablets (dragees), pills, cachets, capsules (caplets), granules, solutions, emulsions and suspensions are e.g. suitable for oral administration. In particular, said formulations can be adapted so as to represent, for example, an enteric form, an immediate release form, a delayed release form, a repeated dose release form, a prolonged release form or a sustained release form. Said forms can be obtained, for example, by coating tablets, by dividing tablets into several compartments separated by layers disintegrating under different conditions (e.g. pH conditions) or by coupling the active compound to a biodegradable polymer.

Administration by inhalation is preferably made by using an aerosol. The aerosol is a liquid-gaseous dispersion, a solid-gaseous dispersion or a mixed liquid/solid-gaseous dispersion.

The aerosol may be generated by means of aerosol-producing devices such as dry powder inhalers (DPIs), pressurized metered dose inhalers (PMDIs) and nebulizers. Depending on the kind of the active compound to be administered, the aerosol-producing device can contain the active compound in form of a powder, a solution or a dispersion. The powder may contain, for example, one or more of the following auxiliaries: carriers, stabilizers and fillers. The solution may contain in addition to the solvent, for example, one or more of the following auxiliaries: propellants, solubilizers (co-solvents), surfactants, stabilizers, buffers, tonicity adjusting agents, preservatives and flavorings. The dispersion may contain in addition to the dispersant, for example, one or more of the following auxiliaries: propellants, surfactants, stabilizers, buffers, preservatives and flavorings. Examples of carriers include, but are not limited to, saccharides, e.g. lactose and glucose. Examples of propellants include, but are not limited to, fluorohydrocarbons, e.g. 1,1,1,2-tetrafluoroethane and 1,1,1,2,3,3,3-heptafluoropropane.

The particle size of the aerosol particles (solid, liquid or solid/liquid particles) is preferably less than 100 μm, more preferably it is in the range of from 0.5 to 10 μm, in particular in the range of from 2 to 6 μm (D50 value, measured by laser diffraction).

For parenteral modes of administration such as, for example, intravenous, intraarterial, intramuscular, subcutaneous, intracutaneous and intraperitoneal administration, preferably solutions (e.g. sterile solutions, isotonic solutions) are used. They are preferably administered by injection or infusion techniques.

The pharmaceutical compositions (formulations) comprising Roflumilast, Roflumilast-N-oxide or a pharmaceutically acceptable salt of either and/or one or more other active compound(s) which are used in the treatment of diabetes mellitus type 2 and/or type 1 and at least one pharmaceutically acceptable auxiliary can be manufactured in a manner known to a person skilled in the art, e.g. by dissolving, mixing, granulating, dragee-making, levigating, emulsifying, encapsulating, entrapping or lyophilizing processes.

As pharmaceutically acceptable auxiliaries, any auxiliaries known to be suitable for preparing pharmaceutical compositions (formulations) can be used. Examples thereof include, but are not limited to, solvents, excipients, dispersants, emulsifiers, solubilizers, gel formers, ointment bases, antioxidants, preservatives, stabilizers, carriers, fillers, binders, thickeners, complexing agents, disintegrating agents, buffers, permeation promoters, polymers, lubricants, coating agents, propellants, tonicity adjusting agents, surfactants, colorants, flavorings, sweeteners and dyes. In particular, auxiliaries of a type appropriate to the desired formulation and the desired mode of administration are used.

The preferred mode of administration of the combinations according to the invention depend on the specific combination partners.

As mentioned above Roflumilast, Roflumilast-N-oxide or a pharmaceutically acceptable salt of either may be administered in a variety of forms. These include, for example, liquid, semi-solid and solid dosage forms, such as liquid solutions (e.g., injectable and infusible solutions), dispersions or suspensions, tablets, pills, powders, liposomes or suppositories. The preferred form depends on the intended mode of administration and the combination partner.

The most preferred mode of administration of Roflumilast, Roflumilast-N-oxide or a pharmaceutically acceptable salt of either is oral. In another preferred embodiment Roflumilast, Roflumilast-N-oxide or a pharmaceutically acceptable salt of either is administered by intravenous infusion or injection. In a further embodiment the Roflumilast, Roflumilast-N-oxide or a pharmaceutically acceptable salt of either is administered by intramuscular or subcutaneous injection. Other routes of administration are also contemplated, including for example intranasal and transdermal routes, and by inhalation.

The preferred mode of administration of the other active compound(s) which is (are) used in combination with Roflumilast, Roflumilast-N-oxide or a pharmaceutically acceptable salt of either depends on the specific agent.

EXENATIDE, BIM-51077, CJC-1131, ZP-10 or PRAMLINTIDE, for example, are preferably administered via subcutaneous injection. The preferred mode of administration of compounds like TOLBUTAMIDE, TOLAZAMIDE, GLIPIZIDE, CARBUTAMIDE, GLISOXEPIDE, GLISENTIDE, GLIBORNURIDE, GLIBENCLAMIDE, GLIQUIDONE, GLIMEPIRIDE, GLICLAZIDE, METFORMIN, ACARBOSE, MIGLITOL, VOGLIBOSE, ROSIGLITAZONE, PIOGLITAZONE, RAGAGLITAZAR, FARGLITAZAR, NAVEGLITAZAR, NETOGLITAZONE, RIVOGLITAZONE, K-111, GW-677954, FK-614, (−)-HALOFENATE, REPAGLINIDE, NATEGLINIDE, MITIGLINIDE, SITAGLIPTIN, SAXAGLIPTIN, VILDAGLIPTIN, DENAGLIPTIN, P32/98, NVP-DPP-728, SILDENAFIL; VARDENAFIL, TADALAFIL, ETOMOXIR, HMR-1426, CETILISTAT and SIBUTRAMINE is oral. Further information with regard to the preferred mode of administration of the other active agent(s) which is (are) used in combination with Roflumilast, Roflumilast-N-oxide or a pharmaceutically acceptable salt of either is summarized in Table 2 below.

As part of the combination therapy according to the invention Roflumilast, Roflumilast-N-oxide or a pharmaceutically acceptable salt of either and the one or more other active compounds which are used in the treatment of diabetes mellitus type 2 and/or type 1 are dosed in an order of magnitude customary for the mono-therapy, it more likely being possible, on account of the individual actions, which are mutually positively influencing and reinforcing, to reduce the respective doses on the combined administration of Roflumilast, Roflumilast-N-oxide or a pharmaceutically acceptable salt of either and the one or more other active compounds which are used in the treatment of diabetes mellitus type 2 and/or type 1 with the norm.

As mentioned above in the case of oral administration of 3-cyclopropylmethoxy-4-difluoromethoxy-N-(3,5-dichloropyrid-4-yl)benzamide (Roflumilast) the daily dose (for an adult patient) for the mono-therapy is in the range from 50 to 500 µg per day, preferably by once daily administration. In the case of intravenous administration of 3-cyclopropylmethoxy-4-difluoromethoxy-N-(3,5-dichloropyrid-4-yl)benzamide (Roflumilast) the daily dose (for an adult patient) is in the range from 50 to 500 µg per day, preferably 150 to 300 µg per day.

Further information with regard to the preferred routes of administration and typical dosages (for mono-therapy) of the other active compound(s) which is (are) used in combination with Roflumilast, Roflumilast-N-oxide or a pharmaceutically acceptable salt of either is summarized in Table 2.

TABLE 2

| INN or Research Code | Preferred Treatment of | Preferred route of Administration | Typical Daily dose (dose ranges) used for mono-therapy |
|---|---|---|---|
| Insulin/ Insulin analogs | Diabetes mellitus type 1 Diabetes mellitus type 2 | subcutaneous injection | On demand |
| EXUBERA | Diabetes mellitus type 1 Diabetes mellitus type 2 | Inhalation | On demand |
| BIM-51077 | Diabetes mellitus type 2 | subcutaneous injection | |
| EXENATIDE | Diabetes mellitus type 2 | subcutaneous injection | 10-20 µg |
| CJC-1131 | Diabetes mellitus type 2 | subcutaneous injection | ≈200 µg |
| ZP-10 | Diabetes mellitus type 2 | subcutaneous injection | |
| TOLBUTAMIDE | Diabetes mellitus type 2 | oral | 0.5 to 2.0 g |
| TOLAZAMIDE | Diabetes mellitus type 2 | oral | 100 to 150 mg |
| GLIPIZIDE | Diabetes mellitus type 2 | oral | 5 to 40 mg, preferably 5 to 20 mg |
| CARBUTAMIDE | Diabetes mellitus type 2 | oral | up to 17 mg/kg |
| GLISOXEPIDE | Diabetes mellitus type 2 | oral | 2 to 16 mg |
| GLISENTIDE | Diabetes mellitus type 2 | oral | |
| GLIBORNURIDE | Diabetes mellitus type 2 | oral | 12.5 to 75 mg |
| GLIBENCLAMIDE | Diabetes mellitus type 2 | oral | 1.75 to 10.5 mg |
| GLIQUIDONE | Diabetes mellitus type 2 | oral | 15 to 120 mg |
| GLIMEPIRIDE | Diabetes mellitus type 2 | oral | 1 to 6 mg |
| GLICLAZIDE | Diabetes mellitus type 2 | oral | 30 to 120 mg |
| METFORMIN | Diabetes mellitus type 2 | oral | 1000 to 3800 mg |
| ACARBOSE | Diabetes mellitus type 2 | oral | 150 to 600 mg, preferably 150 to 300 mg |
| MIGLITOL | Diabetes mellitus type 2 | oral | 150 to 300 mg |
| VOGLIBOSE | Diabetes mellitus type 2 | oral | 0.6 to 0.9 mg |
| MURAGLITAZAR | Diabetes mellitus type 2 | oral or by injection | 2.5 to 5 mg |
| ROSIGLITAZONE | Diabetes mellitus type 2 | oral | 4 to 8 mg |
| PIOGLITAZONE | Diabetes mellitus type 2 | oral | 15 to 45 mg |
| RAGAGLITAZAR | Diabetes mellitus type 2 | oral | 0.1 to 10 mg |
| FARGLITAZAR | Diabetes mellitus type 2 | oral | 0.5 to 10 mg |
| TESAGLITAZAR | Diabetes mellitus type 2 | oral | 0.5 to 1 mg |
| NAVEGLITAZAR | Diabetes mellitus type 2 | oral | 0.004 to 1.2 mg |

TABLE 2-continued

Preferred routes of administration and dosages:

| INN or Research Code | Preferred Treatment of | Preferred route of Administration | Typical Daily dose (dose ranges) used for mono-therapy |
|---|---|---|---|
| NETOGLITAZONE | Diabetes mellitus type 2 | oral | |
| RIVOGLITAZONE | Diabetes mellitus type 2 | oral | |
| K-111 | Diabetes mellitus type 2 | oral | 10 to 20 mg |
| GW-677954 | Diabetes mellitus type 2 | oral | 2.5 to 20 mg |
| FK-614 | Diabetes mellitus type 2 | oral | ≅150 to 200 mg |
| (−)-Halofenate | Diabetes mellitus type 2 | oral | ≅1000 mg |
| REPAGLINIDE | Diabetes mellitus type 2 | oral | 0.5 to 16 mg |
| NATEGLINIDE | Diabetes mellitus type 2 | oral | 180 to 540 mg |
| MITIGLINIDE | Diabetes mellitus type 2 | oral | 40 mg/meal |
| SITAGLIPTIN | Diabetes mellitus type 2 | oral | ≅100 mg |
| SAXAGLIPTIN | Diabetes mellitus type 2 | oral | ≅10 mg |
| VILDAGLIPTIN | Diabetes mellitus type 2 | oral | 25-100 mg |
| DENAGLIPTIN | Diabetes mellitus type 2 | oral | |
| P32/98 | Diabetes mellitus type 2 | oral | |
| NVP-DPP-728 | Diabetes mellitus type 2 | oral | 300 mg |
| SILDENAFIL | Diabetes mellitus type 2 Diabetes mellitus type 1 | oral | 50 to 100 mg |
| VARDENAFIL | Diabetes mellitus type 2 Diabetes mellitus type 1 | oral | 2.5 to 20 mg |
| TADALAFIL | Diabetes mellitus type 2 Diabetes mellitus type 1 | oral | 10 to 20 mg |
| PRAMLINTIDE | Diabetes mellitus type 2 Diabetes mellitus type 1 | subcutaneous injection | 20 to 120 μg |
| ETOMOXIR | Diabetes mellitus type 2 | oral | 10 to 50 mg |
| HMR-1426 | Diabetes mellitus type 2 | oral | |
| CETILISTAT | Diabetes mellitus type 2 | oral | 120 to 920 mg |
| SIBUTRAMINE | Diabetes mellitus type 2 | oral | 10 to 15 mg |

EXAMPLES

TABLE 3

Preferred combinations

| Example Number | Combination | |
|---|---|---|
| 1 | Roflumilast | human insulin |
| 2 | Roflumilast-N-Oxide | human insulin |
| 3 | Roflumilast | Insulin analogue |
| 4 | Roflumilast-N-Oxide | Insulin analogue |
| 5 | Roflumilast | BIM-51077 |
| 6 | Roflumilast-N-Oxide | BIM-51077 |
| 7 | Roflumilast | EXENATIDE |
| 8 | Roflumilast-N-Oxide | EXENATIDE |
| 9 | Roflumilast | CJC-1131 |
| 10 | Roflumilast-N-Oxide | CJC-1131 |
| 11 | Roflumilast | ZP-10 |
| 12 | Roflumilast-N-Oxide | ZP-10 |
| 13 | Roflumilast | TOLBUTAMIDE |
| 14 | Roflumilast-N-Oxide | TOLBUTAMIDE |
| 15 | Roflumilast | TOLBUTAMIDE sodium |
| 16 | Roflumilast-N-Oxide | TOLBUTAMIDE sodium |
| 17 | Roflumilast | TOLAZAMIDE |
| 18 | Roflumilast-N-Oxide | TOLAZAMIDE |
| 19 | Roflumilast | GLIPIZIDE |
| 20 | Roflumilast-N-Oxide | GLIPIZIDE |
| 21 | Roflumilast | CARBUTAMIDE |
| 22 | Roflumilast-N-Oxide | CARBUTAMIDE |
| 23 | Roflumilast | GLISOXEPIDE |
| 24 | Roflumilast-N-Oxide | GLISOXEPIDE |
| 25 | Roflumilast | GLISENTIDE |
| 26 | Roflumilast-N-Oxide | GLISENTIDE |
| 27 | Roflumilast | GLIBORNURIDE |
| 28 | Roflumilast-N-Oxide | GLIBORNURIDE |
| 29 | Roflumilast | GLIBENCLAMIDE |
| 30 | Roflumilast-N-Oxide | GLIBENCLAMIDE |
| 31 | Roflumilast | GLIQUIDONE |
| 32 | Roflumilast-N-Oxide | GLIQUIDONE |
| 33 | Roflumilast | GLIQUIDONE sodium |
| 34 | Roflumilast-N-Oxide | GLIQUIDONE sodium |
| 35 | Roflumilast | GLIMEPIRIDE |
| 36 | Roflumilast-N-Oxide | GLIMEPIRIDE |
| 37 | Roflumilast | GLICLAZIDE |
| 38 | Roflumilast-N-Oxide | GLICLAZIDE |
| 39 | Roflumilast | METFORMIN |
| 40 | Roflumilast-N-Oxide | METFORMIN |
| 41 | Roflumilast | METFORMIN hydrochloride |
| 42 | Roflumilast-N-Oxide | METFORMIN hydrochloride |
| 43 | Roflumilast | ACARBOSE |
| 44 | Roflumilast-N-Oxide | ACARBOSE |
| 45 | Roflumilast | MIGLITOL |
| 46 | Roflumilast-N-Oxide | MIGLITOL |
| 47 | Roflumilast | VOGLIBOSE |
| 48 | Roflumilast-N-Oxide | VOGLIBOSE |
| 49 | Roflumilast | MURAGLITAZAR |
| 50 | Roflumilast-N-Oxide | MURAGLITAZAR |
| 51 | Roflumilast | ROSIGLTAZONE |
| 52 | Roflumilast-N-Oxide | ROSIGLITAZONE |
| 53 | Roflumilast | ROSIGLITAZONE maleate |
| 54 | Roflumilast-N-Oxide | ROSIGLITAZONE maleate |
| 55 | Roflumilast | PIOGLITAZONE |
| 56 | Roflumilast-N-Oxide | PIOGLITAZONE |
| 57 | Roflumilast | PIOGLITAZONE dihydrochloride |
| 58 | Roflumilast-N-Oxide | PIOGLITAZONE dihydrochloride |
| 59 | Roflumilast | RAGAGLITAZAR |
| 60 | Roflumilast-N-Oxide | RAGAGLITAZAR |
| 61 | Roflumilast | FARGLITAZAR |
| 62 | Roflumilast-N-Oxide | FARGLITAZAR |
| 63 | Roflumilast | TESAGLITAZAR |
| 64 | Roflumilast-N-Oxide | TESAGLITAZAR |
| 65 | Roflumilast | NAVEGLITAZAR |
| 66 | Roflumilast-N-Oxide | NAVEGLITAZAR |
| 67 | Roflumilast | NETOGLITAZONE |
| 68 | Roflumilast-N-Oxide | NETOGLITAZONE |
| 69 | Roflumilast | RIVOGLITAZONE |

TABLE 3-continued

Preferred combinations

| Example Number | Combination | |
|---|---|---|
| 70 | Roflumilast-N-Oxide | RIVOGLITAZONE |
| 71 | Roflumilast | RIVOGLITAZONE hydrochloride |
| 72 | Roflumilast-N-Oxide | RIVOGLITAZONE hydrochloride |
| 73 | Roflumilast | K-111 |
| 74 | Roflumilast-N-Oxide | K-111 |
| 75 | Roflumilast | K-111 sodium |
| 76 | Roflumilast-N-Oxide | K-111 sodium |
| 77 | Roflumilast | GW-677954 |
| 78 | Roflumilast-N-Oxide | GW-677954 |
| 79 | Roflumilast | FK-614 |
| 80 | Roflumilast-N-Oxide | FK-614 |
| 81 | Roflumilast | (−)-Halofenate |
| 82 | Roflumilast-N-Oxide | (−)-Halofenate |
| 83 | Roflumilast | REPAGLINIDE |
| 84 | Roflumilast-N-Oxide | REPAGLINIDE |
| 85 | Roflumilast | NATEGLINIDE |
| 86 | Roflumilast-N-Oxide | NATEGLINIDE |
| 87 | Roflumilast | MITIGLINIDE |
| 88 | Roflumilast-N-Oxide | MITIGLINIDE |
| 89 | Roflumilast | MITIGLINIDE potassium |
| 90 | Roflumilast-N-Oxide | MITIGLINIDE potassium |
| 91 | Roflumilast | MITIGLINIDE calcium |
| 92 | Roflumilast-N-Oxide | MITIGLINIDE calcium |
| 93 | Roflumilast | SITAGLIPTIN |
| 94 | Roflumilast-N-Oxide | SITAGLIPTIN |
| 95 | Roflumilast | SITAGLIPTIN phosphate |
| 96 | Roflumilast-N-Oxide | SITAGLIPTIN phosphate |
| 97 | Roflumilast | SAXAGLIPTIN |
| 98 | Roflumilast-N-Oxide | SAXAGLIPTIN |
| 99 | Roflumilast | VILDAGLIPTIN |
| 100 | Roflumilast-N-Oxide | VILDAGLIPTIN |
| 101 | Roflumilast | DENAGLIPTIN |
| 102 | Roflumilast-N-Oxide | DENAGLIPTIN |
| 103 | Roflumilast | P32/98 |
| 104 | Roflumilast-N-Oxide | P32/98 |
| 105 | Roflumilast | P32/98 fumarate |
| 106 | Roflumilast-N-Oxide | P32/98 fumarate |
| 107 | Roflumilast | P32/98 hydrochloride |
| 108 | Roflumilast-N-Oxide | P32/98 hydrochloride |
| 109 | Roflumilast | NVP-DPP-728 |
| 110 | Roflumilast-N-Oxide | NVP-DPP-728 |
| 111 | Roflumilast | SILDENAFIL |
| 112 | Roflumilast-N-Oxide | SILDENAFIL |
| 113 | Roflumilast | SILDENAFIL citrate |
| 114 | Roflumilast-N-Oxide | SILDENAFIL citrate |
| 115 | Roflumilast | SILDENAFIL hemi-citrate |
| 116 | Roflumilast-N-Oxide | SILDENAFIL hemi-citrate |
| 117 | Roflumilast | SILDENAFIL mesilate |
| 118 | Roflumilast-N-Oxide | SILDENAFIL mesilate |
| 119 | Roflumilast | VARDENAFIL |
| 120 | Roflumilast-N-Oxide | VARDENAFIL |
| 121 | Roflumilast | VARDENAFIL hydrochloride |
| 122 | Roflumilast-N-Oxide | VARDENAFIL hydrochloride |
| 123 | Roflumilast | VARDENAFIL dihydrochloride |
| 124 | Roflumilast-N-Oxide | VARDENAFIL dihydrochloride |
| 125 | Roflumilast | TADALAFIL |
| 126 | Roflumilast-N-Oxide | TADALAFIL |
| 127 | Roflumilast | PRAMLINTIDE |
| 128 | Roflumilast-N-Oxide | PRAMLINTIDE |
| 129 | Roflumilast | PRAMLINTIDE acetate |
| 130 | Roflumilast-N-Oxide | PRAMLINTIDE acetate |
| 131 | Roflumilast | ETOMOXIR |
| 132 | Roflumilast-N-Oxide | ETOMOXIR |
| 133 | Roflumilast | HMR-1426 |
| 134 | Roflumilast-N-Oxide | HMR-1426 |
| 135 | Roflumilast | CETILISTAT |
| 136 | Roflumilast-N-Oxide | CETILISTAT |
| 137 | Roflumilast | SIBUTRAMINE |
| 138 | Roflumilast-N-Oxide | SIBUTRAMINE |
| 139 | Roflumilast | SIBUTRAMINE hydrochloride |
| 140 | Roflumilast-N-Oxide | SIBUTRAMINE hydrochloride |

TABLE 4

Preferred triple combinations:

| Example Number | Triple Combination | | |
|---|---|---|---|
| 141 | Roflumilast | METFORMIN | Human Insulin |
| 142 | Roflumilast-N-Oxide | METFORMIN | Human Insulin |
| 143 | Roflumilast | METFORMIN hydrochloride | Human Insulin |
| 144 | Roflumilast-N-Oxide | METFORMIN hydrochloride | Human Insulin |
| 145 | Roflumilast | ROSIGLITAZONE | Human Insulin |
| 146 | Roflumilast-N-Oxide | ROSIGLITAZONE | Human Insulin |
| 147 | Roflumilast | ROSIGLITAZONE maleate | Human Insulin |
| 148 | Roflumilast-N-Oxide | ROSIGLITAZONE maleate | Human Insulin |
| 149 | Roflumilast | ROSIGLITAZONE | METFORMIN |
| 150 | Roflumilast-N-Oxide | ROSIGLITAZONE | METFORMIN |
| 151 | Roflumilast | ROSIGLITAZONE maleate | METFORMIN |
| 152 | Roflumilast-N-Oxide | ROSIGLITAZONE maleate | METFORMIN |
| 153 | Roflumilast | ROSIGLITAZONE maleate | METFORMIN hydrochloride |
| 154 | Roflumilast-N-Oxide | ROSIGLITAZONE maleate | METFORMIN hydrochloride |
| 155 | Roflumilast | PIOGLITAZONE | Insulin |
| 156 | Roflumilast-N-Oxide | PIOGLITAZONE | Insulin |
| 157 | Roflumilast | PIOGLITAZONE dihyrochloride | Insulin |
| 158 | Roflumilast-N-Oxide | PIOGLITAZONE dihyrochloride | Insulin |
| 159 | Roflumilast | PIOGLITAZONE | METFORMIN |
| 160 | Roflumilast-N-Oxide | PIOGLITAZONE | METFORMIN |
| 161 | Roflumilast | PIOGLITAZONE | METFORMIN hydrochloride |

TABLE 4-continued

Preferred triple combinations:

| Example Number | | Triple Combination | |
|---|---|---|---|
| 162 | Roflumilast-N-Oxide | PIOGLITAZONE | METFORMIN hydrochloride |
| 163 | Roflumilast | PIOGLITAZONE dihyrochloride | METFORMIN |
| 164 | Roflumilast-N-Oxide | PIOGLITAZONE dihyrochloride | METFORMIN |
| 165 | Roflumilast | PIOGLITAZONE dihyrochloride | METFORMIN hydrochloride |
| 166 | Roflumilast-N-Oxide | PIOGLITAZONE dihyrochloride | METFORMIN hydrochloride |
| 167 | Roflumilast | GLIMEPIRIDE | Insulin |
| 168 | Roflumilast-N-Oxide | GLIMEPIRIDE | Insulin |
| 169 | Roflumilast | GLIMEPIRIDE | METFORMIN |
| 170 | Roflumilast-N-Oxide | GLIMEPIRIDE | METFORMIN |
| 171 | Roflumilast | GLIMEPIRIDE | METFORMIN hydrochloride |
| 172 | Roflumilast-N-Oxide | GLIMEPIRIDE | METFORMIN hydrochloride |
| 173 | Roflumilast | GLIMEPIRIDE | ROSIGLITAZONE |
| 174 | Roflumilast-N-Oxide | GLIMEPIRIDE | ROSIGLITAZONE |
| 175 | Roflumilast | GLIMEPIRIDE | ROSIGLTAZONE maleate |
| 176 | Roflumilast-N-Oxide | GLIMEPIRIDE | ROSIGLITAZONE maleate |
| 177 | Roflumilast | GLIMEPIRIDE | PIOGLITAZONE |
| 178 | Roflumilast-N-Oxide | GLIMEPIRIDE | PIOGLITAZONE |
| 179 | Roflumilast | GLIMEPIRIDE | PIOGLITAZONE dihydrochloride |
| 180 | Roflumilast-N-Oxide | GLIMEPIRIDE | PIOGLITAZONE dihydrochloride |

Pharmacology (Mono-Therapy)

Model

Female C57BLKS db/db mice obtained from M&B NS (8680 Ry, Denmark) were used in the studies at 10 to 11 weeks of age. Mice were housed 10 per cage and allowed free access to water and standard laboratory diet for rodents (chow 3433, Provimi Kliba SA, 4303 Kaiseraugst, Switzerland).

Experimental Protocol

Mice were allowed to acclimate to the local animal facilities for 1 week and retro-orbital blood samples were obtained 3 to 7 days prior to the start of the study.

Mice were treated with vehicle, Roflumilast or Roflumilast-N-Oxide, respectively once daily in the morning. Roflumilast or Roflumilast-N-Oxide was suspended in 4% methocel and applied via oral gavage using oral feeding & dosing needles (outer diameter: 1.5 mm, TSE GmbH, 61350 Bad Homburg, Germany). A volume of 10 ml/kg body weight was administered for each dose.

The daily intake of food (chow 3433) and water was measured per animal (total daily intake of food divided by the number of animals) before and during the treatment with Roflumilast or Roflumilast-N-Oxide.

10 Days Studies:

Mice were treated with vehicle, Roflumilast or Roflumilast-N-Oxide once daily in the morning. On day 9, mice were fasted for 24 hours by removing standard diet for laboratory animals 1 hour after drug application. On day 10, one hour after administration of vehicle, Roflumilast or Roflumilast-N-Oxide glucose tolerance was assessed by oral application of 1 g/kg/10 ml glucose. Blood was sampled before and 15 minutes after glucose application and levels of glucose (accuchek, Roche Diagnostics GmbH, 68298 Mannheim, Germany) were measured.

Results

Table 5 illustrates food intake of the mice on the days (24 h time periods) before and during application of Roflumilast-N-Oxide:

TABLE 5

| | Daily food intake [g per mouse] on the days (24 h time periods) before the first application of vehicle, respectively Rof-N-Oxide | | | | | Daily food intake [g per mouse] on the days (24 h time periods) of application of vehicle, respectively Rof-N-Oxide | | | | | | | |
|---|---|---|---|---|---|---|---|---|---|---|---|---|---|
| Day | −5 | −4 | −3 | −2 | −1 | 1 | 2 | 3 | 4 | 5 | 6 | 7 | 8 |
| Vehicle (4% methocel) | 5.2 | 5.7 | 5.8 | 5.6 | 5.7 | 5.7 | 5.4 | 5.5 | 5.5 | 5.8 | 5.9 | 5.1 | 5.1 |
| Rof-N-Oxide - 1 mg/kg | 6.0 | 5.9 | 6.4 | 6.4 | 6.4 | 5.4 | 5.4 | 5.8 | 5.5 | 5.6 | 5.8 | 5.4 | 5.5 |
| Rof-N-Oxide - 3 mg/kg | 5.5 | 6.4 | 6.4 | 6.1 | 6.1 | 4.9 | 4.9 | 4.5 | 4.5 | 4.6 | 4.9 | 4.3 | 4.2 |
| Rof-N-Oxide - 10 mg/kg | 6.0 | 6.2 | 6.4 | 6.4 | 6.5 | 2.9 | 3.3 | 3.5 | 2.9 | 3.0 | 3.1 | 2.6 | 3.8 |
| Rof-N-Oxide - 30 mg/kg | 5.8 | 6.4 | 6.5 | 6.2 | 6.3 | 1.4 | 0.9 | 1.2 | 0.8 | 0.9 | 1.1 | 0.7 | 0.6 |

[Day "−1" means the 24 h time period before the first application of vehicle/Roflumilast-N-Oxide; Day "1" means means the 24 h time period after first application of vehicle/Roflumilast-N-Oxide; Day "2" means the 24 h time period after the second application of vehicle/Roflumilast-N-Oxide; and so on]

Table 6 illustrates water intake of the mice on the days (24 h time periods) before and during application of Roflumilast-N-Oxide.

TABLE 6

|  | \multicolumn{5}{c}{Daily water intake [g per mouse] on the days (24 h time periods) before the first application of vehicle, respectively Rof-N-Oxide} | \multicolumn{8}{c}{Daily water intake [g per mouse] on the days (24 h time periods) of application of vehicle, respectively Rof-N-Oxide} |
|---|---|---|---|---|---|---|---|---|---|---|---|---|---|
|  | \multicolumn{13}{c}{Days} |
|  | −5 | −4 | −3 | −2 | −1 | 1 | 2 | 3 | 4 | 5 | 6 | 7 | 8 |
| Vehicle (4% methocel) | 7.9 | 8.8 | 6.5 | 6.9 | 6.7 | 7.2 | 7.7 | * | 9.0 | 8.5 | 8.1 | 7.9 | 8.1 |
| Rof-N-Oxide - 1 mg/kg | 9.2 | 9.4 | 8.4 | 7.9 | 8.6 | 7.6 | 6.9 | * | 7.1 | 8.0 | 7.7 | 8.5 | 7.2 |
| Rof-N-Oxide - 3 mg/kg | 9.8 | 4.3 | 7.6 | 7.6 | 9.1 | 5.1 | 5.9 | * | 5.9 | 5.7 | 5.4 | 5.4 | 5.2 |
| Rof-N-Oxide - 10 mg/kg | 12.1 | 9.6 | 7.9 | 8.2 | 9.6 | 2.9 | 3.5 | * | 3.2 | 3.7 | 3.3 | 3.0 | 4.1 |
| Rof-N-Oxide - 30 mg/kg | 10.1 | 12.4 | 10.0 | 9.4 | 10.1 | 2.3 | 2.4 | * | 2.6 | 3.0 | 2.9 | 3.3 | 2.5 |

* no value due to technical artefact
[Day "−1" means the 24 h time period before the first application of vehicle/Roflumilast-N-Oxide; Day "1" means means the 24 h time period after first application of vehicle/Roflumilast-N-Oxide; Day "2" means the 24 h time period after the second application of vehicle/Roflumilast-N-Oxide; and so on]

Table 7 illustrates blood glucose levels before and 15 minutes after glucose application.

Mice were treated 10 days with Roflumilast.

TABLE 7

| | Blood glucose [mg/dl] (before glucose application) | Blood glucose [mg/dl] (15 min after glucose application) |
|---|---|---|
| Vehicle (4% methocel) | 360 | 574 |
| Roflumilast - 1 mg/kg | 347 | 507 |
| Roflumilast - 10 mg/kg | 191 | 412 |

Table 8 illustrates blood glucose levels before and 15 minutes after glucose application.

Mice were treated 10 days with Roflumilast-N-oxide (=Rof-N-Oxide)

TABLE 8

| | Blood glucose [mg/dl] (before glucose application) | Blood glucose [mg/dl] (15 min after glucose application) |
|---|---|---|
| Vehicle (4% methocel) | 301 | 533 |
| Rof-N-Oxide - 1 mg/kg | 220 | 595 |
| Rof-N-Oxide - 3 mg/kg | 174 | 467 |
| Rof-N-Oxide - 10 mg/kg | 139 | 423 |
| Rof-N-Oxide - 30 mg/kg | 146 | 326 |

SUMMARY

Treatment with Roflumilast-N-oxide has been demonstrated to reduce in a dose-dependent manner the daily food intake in db/db mice. Additionally, the increased daily water intake in db/db mice due to glucosuria, which is a result of high blood glucose levels, was reduced during treatment with Roflumilast-N-oxide. Furthermore, treatment with Roflumilast or Roflumilast-N-oxide has been demonstrated to reduce fasting and postprandial blood glucose levels in db/db mice in accordance with the biochemical test methods detailed hereinbefore.

The invention claimed is:
1. A pharmaceutical composition comprising a pharmaceutical formulation including a first amount of a compound of formula 1.1

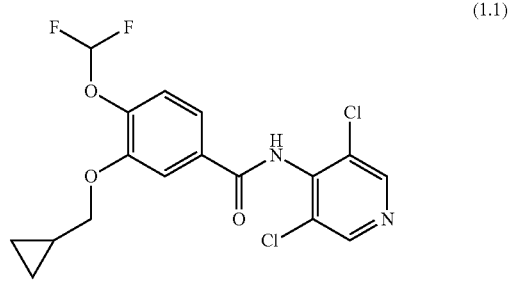 [SMILES: O=C(Nc1c(Cl)cncc1Cl)c1ccc(OC(F)F)c(OCC2CC2)c1]

(1.1)

or a pharmaceutically acceptable salt thereof and/or a compound of formula 1.2

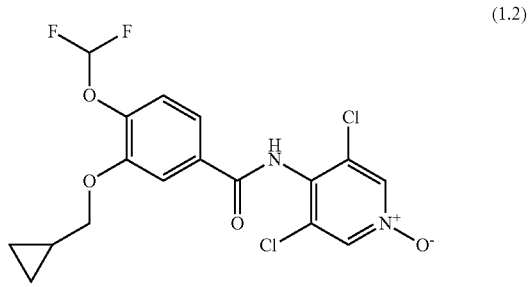 [SMILES: O=C(Nc1c(Cl)c[n+]([O-])cc1Cl)c1ccc(OC(F)F)c(OCC2CC2)c1]

(1.2)

or a pharmaceutically acceptable salt thereof, a second amount of a PPAR-agonist selected from the group consisting of MURAGLITAZAR, ROSIGLITAZONE, PIOGLITAZONE, RAGAGLITAZAR, FARGLITAZAR, TESAGLITAZAR, NAVEGLITAZAR, NETOGLITAZONE, RIVOGLITAZONE, K-111, GW-677954, FK-614, (−)-Halofenate and the pharmaceutically acceptable salts of these compounds, wherein the first amount and the second amount together comprise an effective amount for the treatment of diabetes mellitus type 2, and at least one pharmaceutically acceptable auxiliary.

2. The pharmaceutical composition according to claim 1, wherein the PPAR-agonist is selected from the group consisting of PIOGLITAZONE and the pharmaceutically acceptable salts thereof.

3. The pharmaceutical composition according to claim 1, wherein the pharmaceutical formulation is a combination of Roflumilast and PIOGLITAZONE.

4. The pharmaceutical composition according to claim 1, wherein the pharmaceutical formulation is a combination of Roflumilast and a pharmaceutically acceptable salt of PIOGLITAZONE.

5. A method for treating diabetes mellitus type 2 comprising administering to a patient in need thereof a pharmaceutical composition comprising a pharmaceutical formulation including a first amount of a compound of formula 1.1

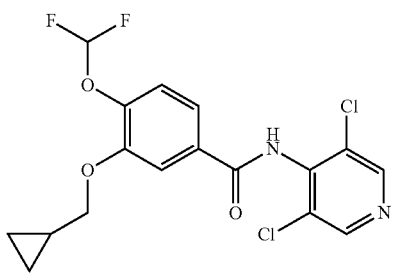

(1.1)

or a pharmaceutically acceptable salt thereof and/or a compound of formula 1.2

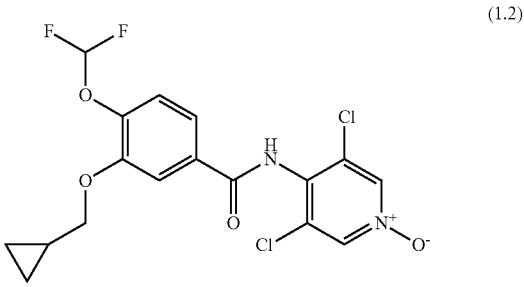 [SMILES: O=C(Nc1c(Cl)c[n+]([O-])cc1Cl)c1ccc(OC(F)F)c(OCC2CC2)c1]

(1.2)

or a pharmaceutically acceptable salt thereof, a second amount of a PPAR-agonist selected from the group consisting of MURAGLITAZAR, ROSIGLITAZONE, PIOGLITAZONE, RAGAGLITAZAR, FARGLITAZAR, TESAGLITAZAR, NAVEGLITAZAR, NETOGLITAZONE, RIVOGLITAZONE, K-111, GW-677954, FK-614, (−)-Halofenate and the pharmaceutically acceptable salts of these compounds, wherein the first amount and the second amount together comprise an effective amount for the treatment of diabetes mellitus type 2, and at least one pharmaceutically acceptable auxiliary.

6. The method according to claim 5, wherein the PPAR-agonist is selected from the group consisting of PIOGLITAZONE and the pharmaceutically acceptable salts thereof.

7. The method according to claim 5, wherein the pharmaceutical formulation is a combination of Roflumilast and PIOGLITAZONE.

8. The method according to claim 5, wherein the pharmaceutical formulation is a combination of Roflumilast and a pharmaceutically acceptable salt of PIOGLITAZONE.

* * * * *